(12) United States Patent
Asao et al.

(10) Patent No.: US 9,562,920 B2
(45) Date of Patent: Feb. 7, 2017

(54) AUTOMATED ANALYZER WITH COVER DETECTION

(71) Applicant: Sysmex Corporation, Kobe-shi, Hyogo (JP)

(72) Inventors: Kazuki Asao, Kobe (JP); Tsukasa Hirata, Kobe (JP)

(73) Assignee: Sysmex Corporation (JP)

( * ) Notice: Subject to any disclaimer, the term of this patent is extended or adjusted under 35 U.S.C. 154(b) by 183 days.

(21) Appl. No.: 14/496,714

(22) Filed: Sep. 25, 2014

(65) Prior Publication Data

US 2015/0093754 A1 Apr. 2, 2015

(30) Foreign Application Priority Data

Sep. 27, 2013 (JP) ................................. 2013-201175

(51) Int. Cl.
| | |
|---|---|
| *G01N 35/10* | (2006.01) |
| *B01L 9/00* | (2006.01) |
| *G01N 35/00* | (2006.01) |
| *G01N 35/04* | (2006.01) |

(52) U.S. Cl.
CPC .......... *G01N 35/1009* (2013.01); *B01L 9/543* (2013.01); *G01N 35/1011* (2013.01); *G01N 35/1065* (2013.01); *B01L 2300/046* (2013.01); *B01L 2300/0627* (2013.01); *G01N 2035/0091* (2013.01); *G01N 2035/00287* (2013.01); *G01N 2035/00316* (2013.01); *G01N 2035/0405* (2013.01); *G01N 2035/103* (2013.01); *G01N 2035/1013* (2013.01); *Y10T 436/115831* (2015.01)

(58) Field of Classification Search
None
See application file for complete search history.

(56) References Cited

U.S. PATENT DOCUMENTS

| | | | |
|---|---|---|---|
| 2006/0093530 A1* | 5/2006 | Ueda ....................... | B01L 9/543 422/400 |
| 2008/0011106 A1* | 1/2008 | Kitagawa ............. | G01N 35/025 73/863 |
| 2011/0269239 A1* | 11/2011 | Diessel ................ | G01N 35/028 436/43 |

\* cited by examiner

*Primary Examiner* — Sean E Conley
*Assistant Examiner* — Benjamin R Whatley
(74) *Attorney, Agent, or Firm* — Brinks Gilson & Lione

(57) ABSTRACT

Disclosed is an analyzer comprising: a liquid container mounting section in which a liquid container are set; a container mounting section in which at least one tip container accommodating a plurality of pipette tips is set; a cover detecting section that detects a presence of a cover mounted on the tip container; a dispensing section that equips a pipette tip accommodated in the tip container and dispenses a quantity of liquid from the liquid container to a reaction container via the equipped pipette tip; a detecting section that interrogate a property of the liquid; and a controller programmed to prohibit a process of equipping the pipette tip by the dispensing section when the cover on the tip container is detected, and permits the process when no cover is detected.

10 Claims, 25 Drawing Sheets

AUTOMATED ANALYZER WITH COVER DETECTION

RELATED APPLICATIONS

This application claims priority under 35 U.S.C. §119 to Japanese Patent Application No. 2013-201175 filed on Sep. 27, 2013, the entire content of which is hereby incorporated by reference.

FIELD OF THE INVENTION

The present invention relates to an analyzer, analyzing method, and tip container used in the analyzing method.

BACKGROUND OF THE INVENTION

Conventional analyzer which is detachably installed with a rack containing a plurality of pipette tips is known (see U.S. Patent Application Publication No. 2005-0178795).

Before being set in the analyzer, the rack is stored in a state wherein upper and lower covers are mounted. When performing measurements, the user removes the upper cover after the rack is set, and issues an instruction to start the measurement.

In the conventional analyzer, if the user fails to remove the upper cover before a measurement starts, a dispensing unit comes into contact with the upper cover when moving to the rack in order to equip the pipette tip, and an error is generated. In such case, a considerable time must be consumed to cancel the error and to make a recovery process.

SUMMARY OF THE INVENTION

A first aspect of the present invention is an analyzer comprising: a liquid container mounting section in which a liquid container are set; a container mounting section in which at least one tip container accommodating a plurality of pipette tips is set; a cover detecting section that detects a presence of a cover mounted on the tip container; a dispensing section that equips a pipette tip accommodated in the tip container and dispenses a quantity of liquid from the liquid container to a reaction container via the equipped pipette tip; a detecting section that interrogate a property of the liquid; and a controller programmed to prohibit a process of equipping the pipette tip by the dispensing section when the cover on the tip container is detected, and permits the process when no cover is detected.

A second aspect of the present invention is a method implemented in an analyzer, comprising: at an analyzer installed with a liquid container, a reaction container and a tip container accommodating a plurality of pipette tips, receiving an instruction to start a measurement; detecting a presence or absence of a cover mounted on the tip container in response to the instruction; carrying out, when no cover is detected, an operation comprising: equipping a dispensing section of the analyzer with a pipette tip in the tip container when no cover is detected; dispensing a quantity of liquid from the liquid container to the reaction container via the pipette tip; and interrogating a property of the liquid in the reaction container, and avoiding the operation when a cover is detected.

A third aspect of the present invention is a tip container installed to and used by the analyzer in the above mentioned method, comprising: a main container body capable of accommodating a plurality of pipette tips; and a cover mounted on the tip container main body; wherein the cover has a detection part to be detected by the analyzer.

DETAILED DESCRIPTION OF THE PREFERRED EMBODIMENTS

First Embodiment

The first embodiment of the present invention is hereinafter described with reference to the appended drawings.

The general structures of the gene amplification detecting apparatus 100 and the tip container 1 are described below referring to FIGS. 1 through 19.

The gene amplification detecting apparatus 100 (see FIG. 1) is used to support a diagnosis of cancer metastasis in surgically excised tissue. The gene amplification detecting apparatus 100 is configured to amplify cancer genes present in the excised tissue using the LAMP (loop mediated isothermal amplification) method, and measure (detect) the turbidity of the liquid produced in conjunction with the amplification of the genes. Details of the LAMP method are disclosed in U.S. Pat. No. 6,410,278.

The tip container 1 (see FIG. 2) which accommodates pipette tips (hereinafter referred to as "tips") 150 (see FIG. 3) is arranged in the gene amplification detecting apparatus 100. The structure of the tip container 1 is described next below, followed by a description of the structure of the gene amplification detecting apparatus 100.

Figure 1:
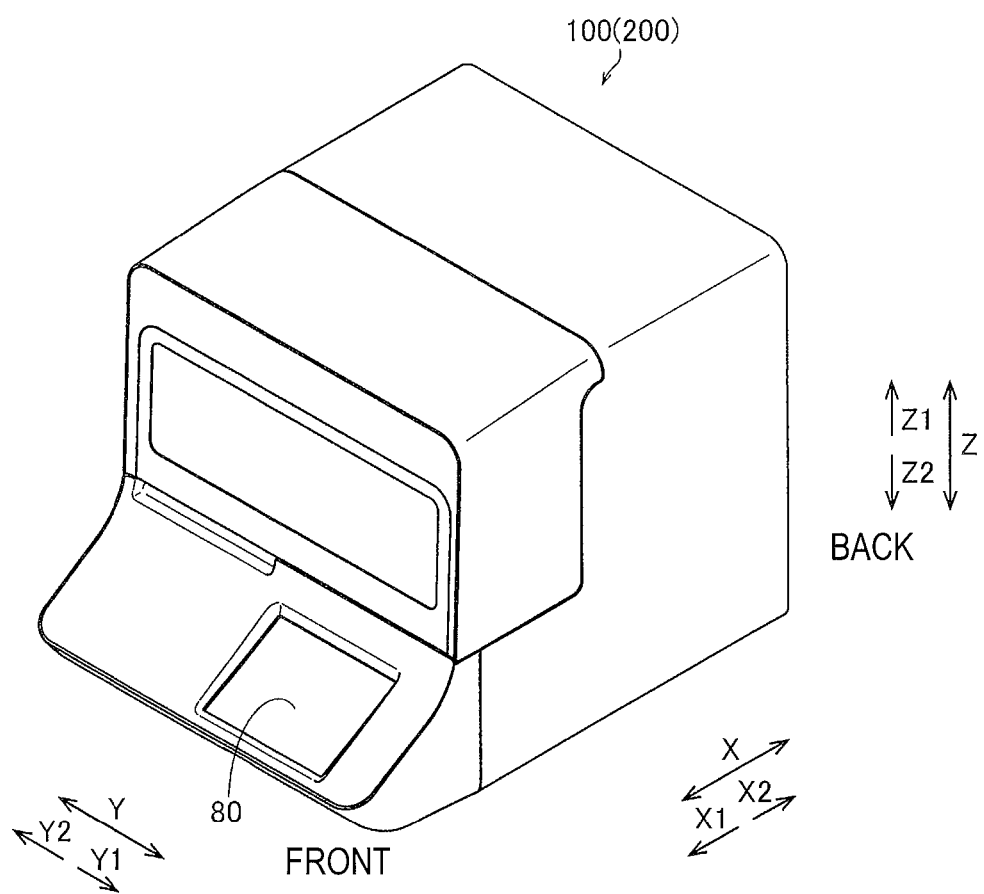
FIG. 1 is a perspective view of a gene amplification detection apparatus of a first embodiment.
Figure 2:
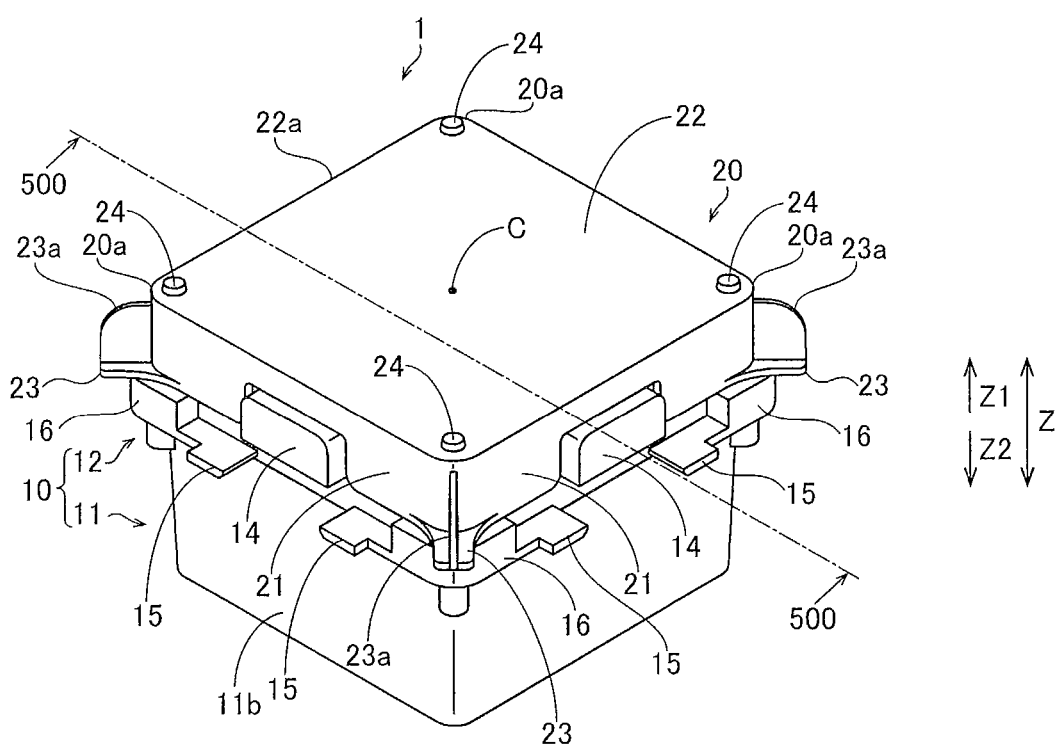
FIG. 2 is a perspective view of the tip container of the first embodiment.
Figure 3:
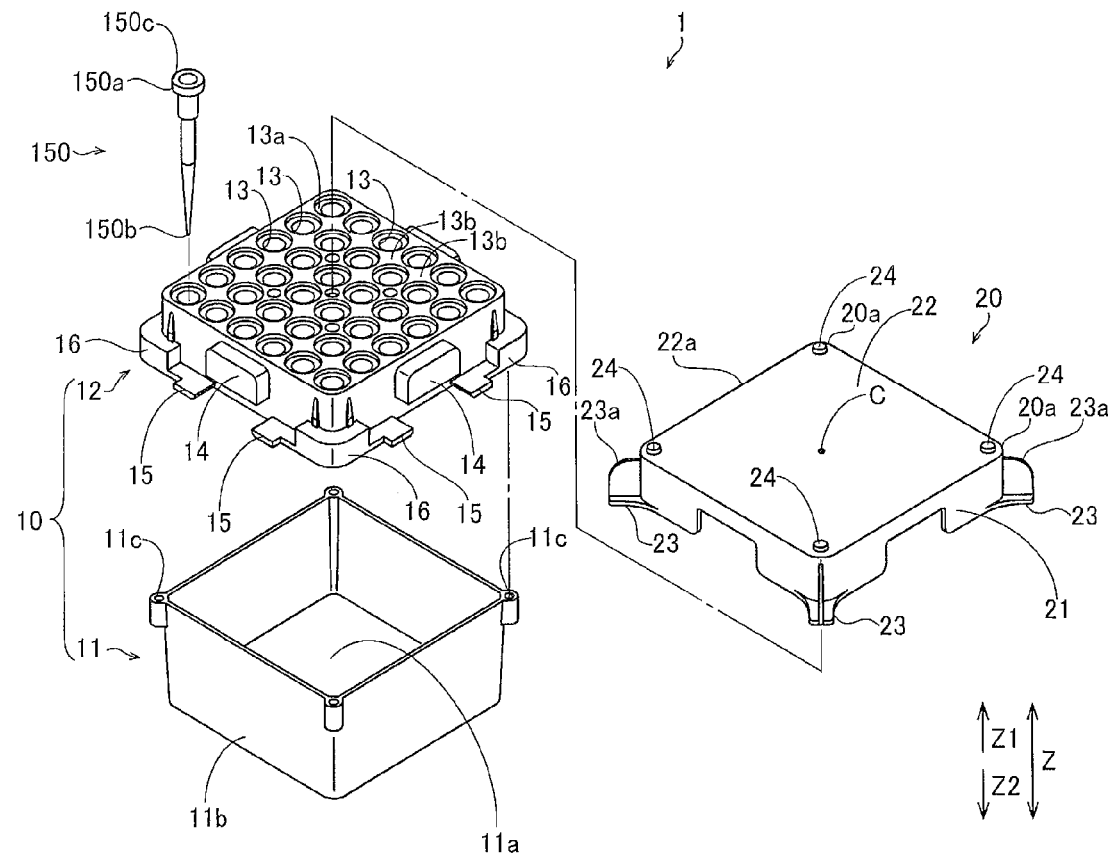
FIG. 3 is an exploded perspective view of the tip container of the first embodiment.

The tip container 1 includes a tip container body 10 and a cover 20 as shown in FIGS. 2 and 3. The material of the tip container 1 is not specifically limited and may be, for example, a resin material. In the first embodiment, the tip 150 accommodated in the tip container 1 is formed of a conductive resin material containing carbon, and a filter is installed on the inside to prevent an erroneous influx of liquid. The tip 150 is tapered from the base part 150c toward the tip part 150b. A collar 150a is formed on the base part 150c of the tip 150. Note that the material of the tip 150 is not specifically limited to conductive resin material.

Figure 4:
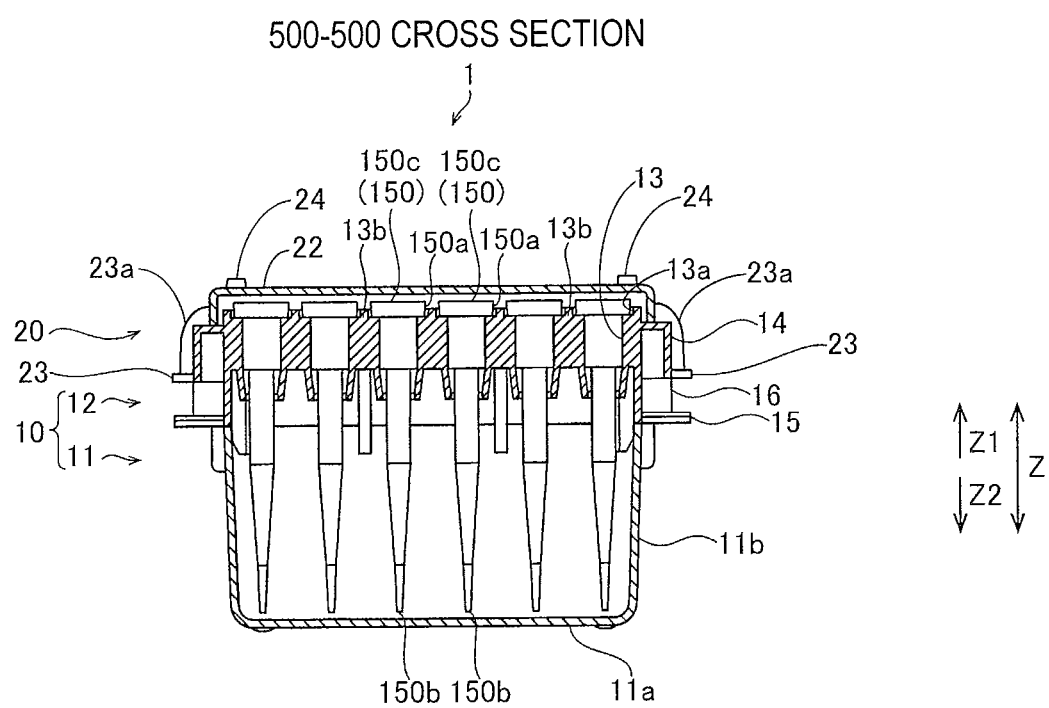
FIG. 4 is a cross sectional view on the 500-500 line of FIG. 2.

The tip container body 10 includes a tip support (hereinafter "support") 12 which supports the tip 150 so as to be removable, and a tip holding part (hereinafter "holder") 11 which accommodates the tip part 150b of the tip 150 supported by the support part 12, as shown in FIGS. 3 and 4.

The holder 11 is configured by a bottom part 11a and side part 11b. Specifically, the holder 11 has a substantially rectangular box-like shape with a substantially open top surface. The holder 11 is configured to be disposed below the support 12. Holes 11c are provided at the respective top ends of the four corners of the holder 11.

The support 12 includes tip insertion holes (hereinafter "insertion hole") 13, gripper 14, fixing part 15, and reinforcing rib 16. The tip 150 is able to be inserted in the insertion hole 13. Thirty-six insertion holes 13 are arranged in a 6×6 matrix. Each insertion hole 13 is cylindrical in shape extending downward from the top surface of the support 12. The insertion hole 13 has a stepped portion 13a near the opening. The stepped portion 13a is configured to fit the collar 150a of the tip 150. The reinforcing ribs 13b are formed between mutually adjacent insertion holes 13.

Figure 5:
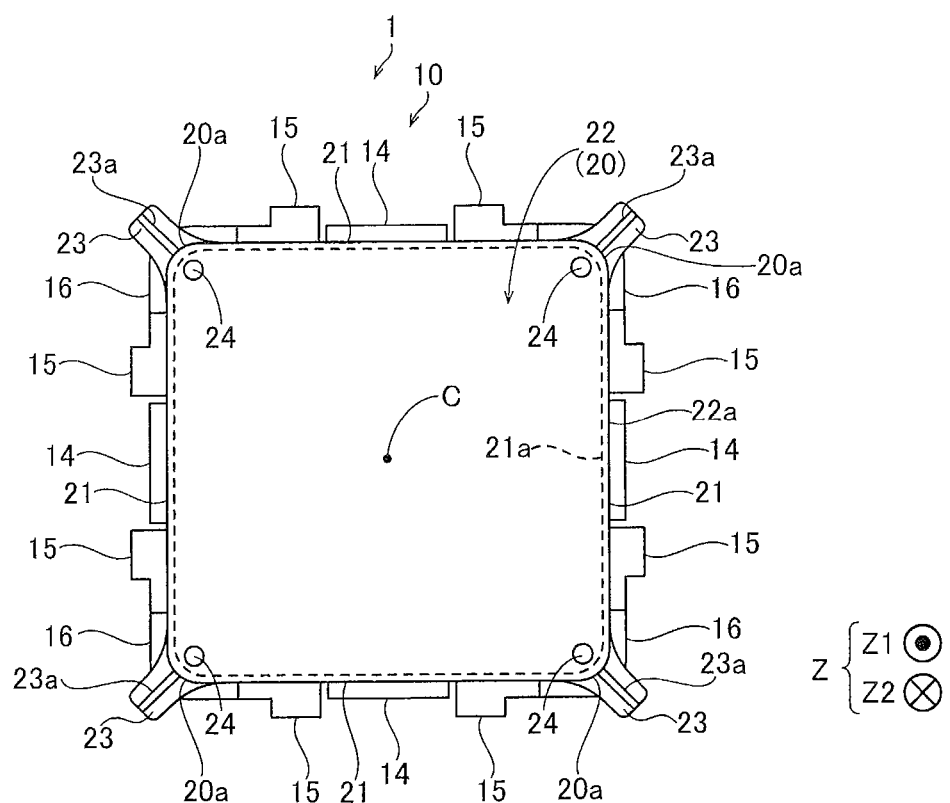
FIG. 5 is a top view of the tip container of the first embodiment.

The grippers 14 are formed individually at the center of each of the four sides of the support 12, as shown in FIG. 5. The respective grippers 14 are configured so as to protrude to the outside from the side surface 21 of the cover 20 when the cover 20 is mounted on the tip container body 10.

The fixing part 15 is provided in pairs on each of the four sides of the support 12. As shown in FIG. 3, the fixing part 15 is configured so as to protrude in a lateral direction from the bottom end position of the side surface of the support 12.

As shown in FIG. 5, the reinforcing rib 16 is provided individually at the four corners of the support 12. Specifically, the reinforcing ribs 16 are configured so as to protrude to the outside from the bottom end position of the corners formed by the meeting of two adjacent sides of the support 12. The reinforcing ribs 16 connect the two fixing parts 15 on the two adjacent sides. A projecting part (not shown in the drawings) also is formed on the bottom end of the respective four reinforcing ribs 16. The support 12 is detachably mounted on the holder 11 when the projecting part engages the hole 11c of the holder 11.

The cover 20 is configured to be removably fitted to the top part of the tip container body 10. Hence, the top part of the tip container body 10 is easily covered by the cover 20. As shown in FIG. 4, the cover 20 is configured to cover the base part 150c of the tip 150 inserted into the insertion hole 13 of the support 12. The cover 20 integratedly includes the side surface 21, top surface 22, detection part 23, and convexity 24.

The side surface 21 extends downward from the edge 22a of the top surface 22.

As shown in FIG. 5, the top surface 22 is substantially square in shape in planar view.

The detection part 23 is provided on all four corners 20a of the cover 20. The detection part 23 extends laterally to the outside from the side surface 21. The bottom end (side in the Z2 direction) of the detection part 23 is a flat surface, extending approximately parallel (XY plane) to the top surface 22. The detection part 23 is provided at a position lower than the top surface 22 of the cover 20. Specifically, the detection part 23 is provided near the bottom end of the side surface 21, as shown in FIG. 4. The detection part 23 protrudes to the outside more than the fixing part 15 and the reinforcing rib 16 of the tip container body 10, as shown in FIG. 5. A cover detector 34 detects the presence or absence of the detection part 23 at a position corresponding to the cover detector 34 (described later) for all detection parts 23 provided on the cover 20. Hence, the presence or absence of the cover 20 on the tip container body 10 can be detected.

As shown in FIG. 2, the detection part 23 has a reinforcing rib 23a. The reinforcing rib 23a extends approximately perpendicular to the detection part 23. The reinforcing rib 23a is provided at a lower position than the top surface 22 of the cover 20. Specifically, the reinforcing rib 23a is provided near the bottom end of the side surface 21, as shown in FIG. 4. The reinforcing rib 23a extends on a straight line from the opposite corner of the substantially square shaped top surface 22. The reinforcing rib 23a passes through the vicinity of the center of the detection part 23.

Figure 6:
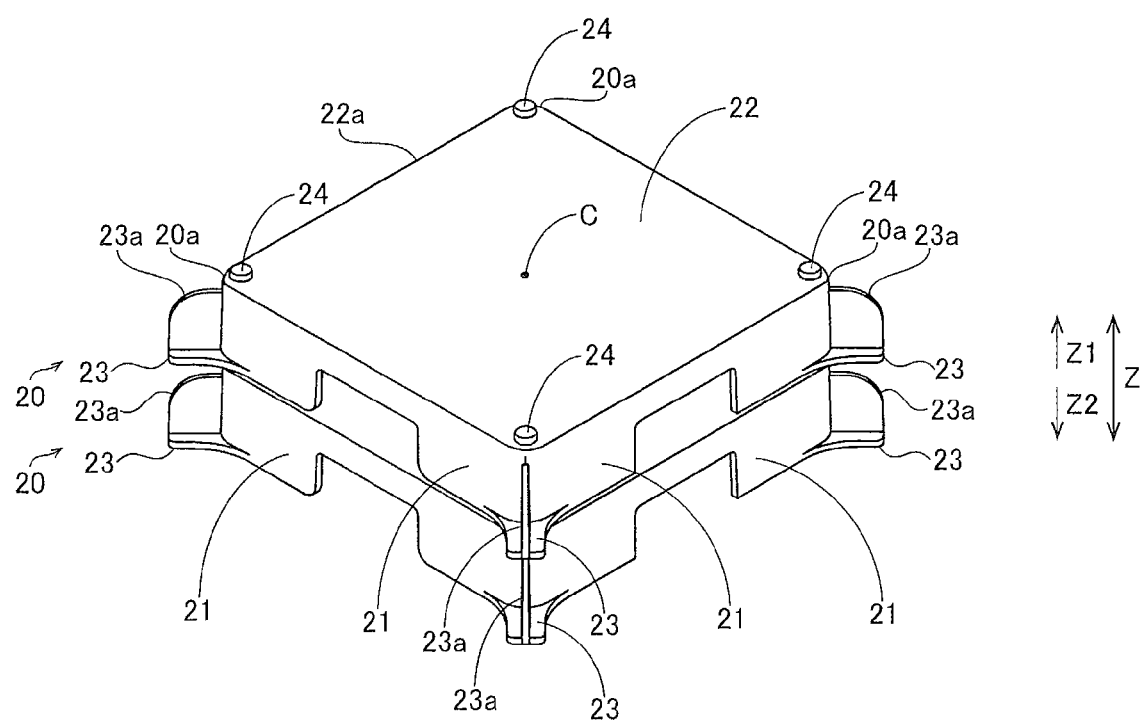
FIG. 6 illustrates the stacked tip container covers of the first embodiment.

Four convexities 24 are provided on the top surface 22 so as to protrude upward. The four convexities 24 are disposed near the respective corners 20a of the cover 20. In planar view, the four convexities 24 are disposed near the inner surface 21a of the side surface 21. When a plurality of covers 20 are stacked as shown in FIG. 6, the plurality of convexities 24 of one cover 10 mutual engage the side surface (inner surface 21a; refer to FIG. 5) of the other cover 20.

The structure of the gene amplification detecting apparatus 100 is described below.

Figure 7:
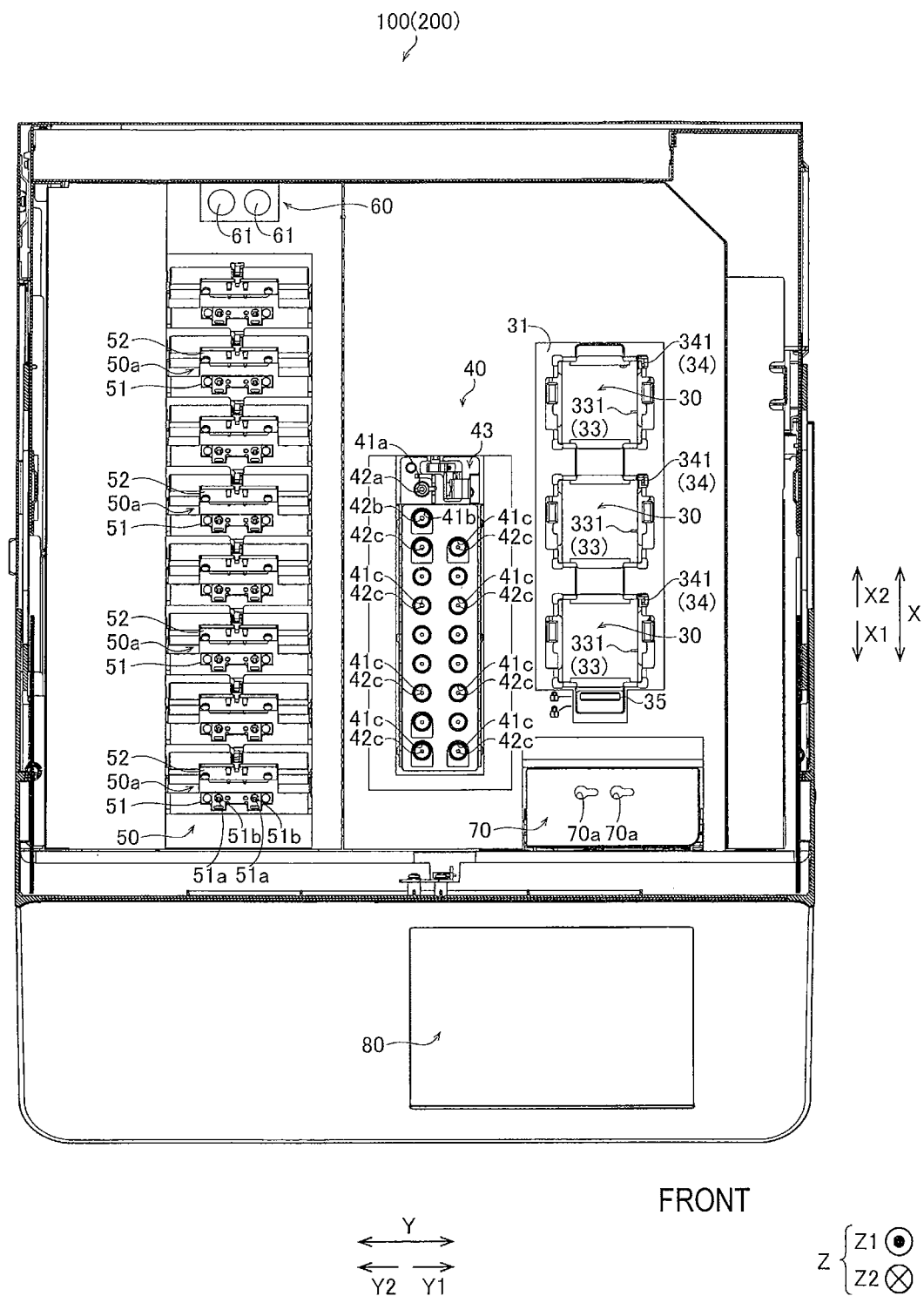
FIG. 7 shows the inside of the gene amplification detecting apparatus of the first embodiment.

The gene amplification detecting apparatus 100 includes a tip container mounting section 30 in which are mounted tip containers 1, a liquid container mounting section 40, and reaction detecting section 50, as shown in FIG. 7. The gene amplification detecting apparatus 100 also includes a dispensing section 60, tip disposal section 70, touch panel 80, a CPU 90 (see FIG. 8) which controls the gene amplification detecting apparatus 100.

Figure 9:
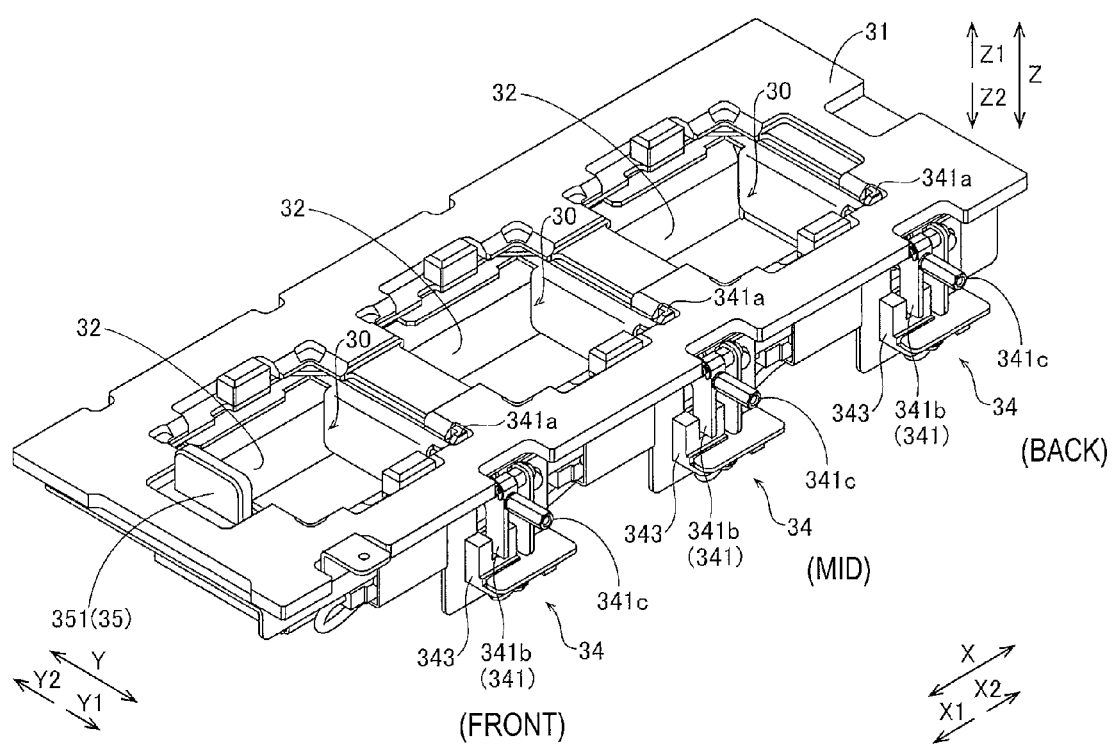
FIG. 9 shows the tip container mounting section of the gene amplification detecting apparatus of the first embodiment.
Figure 10:
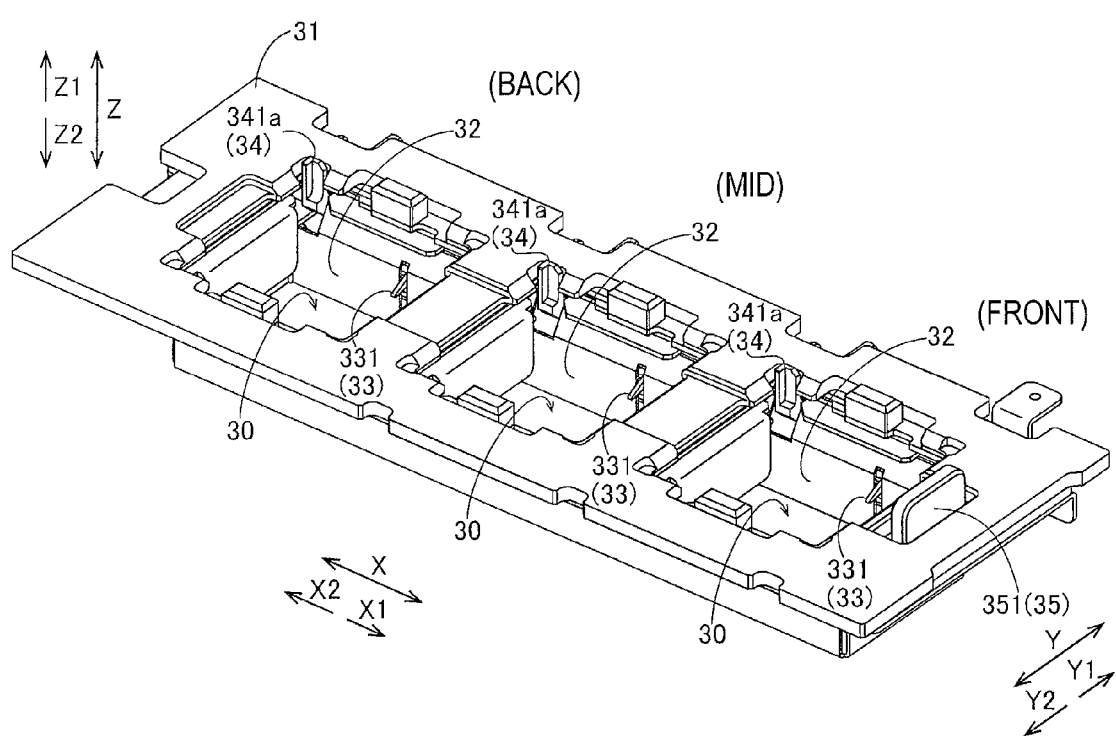
FIG. 10 shows the main detecting section of the gene amplification detecting apparatus of the first embodiment.

Three tip container mounting sections 30 are provided on a set rack 31, as shown in FIGS. 9 and 10. The tip container mounting section 30 is provided with an open part 32, body detecting section 33, cover detecting section 34, and fixing mechanism 35. The tip container body of the tip container 1 can be mounted in the tip container mounting section 30. Note that the respective placement positions of the three tip container mounting sections 30 are sequential from the back side (X2 direction side) in the order "back," "middle," "front."

Figure 11:
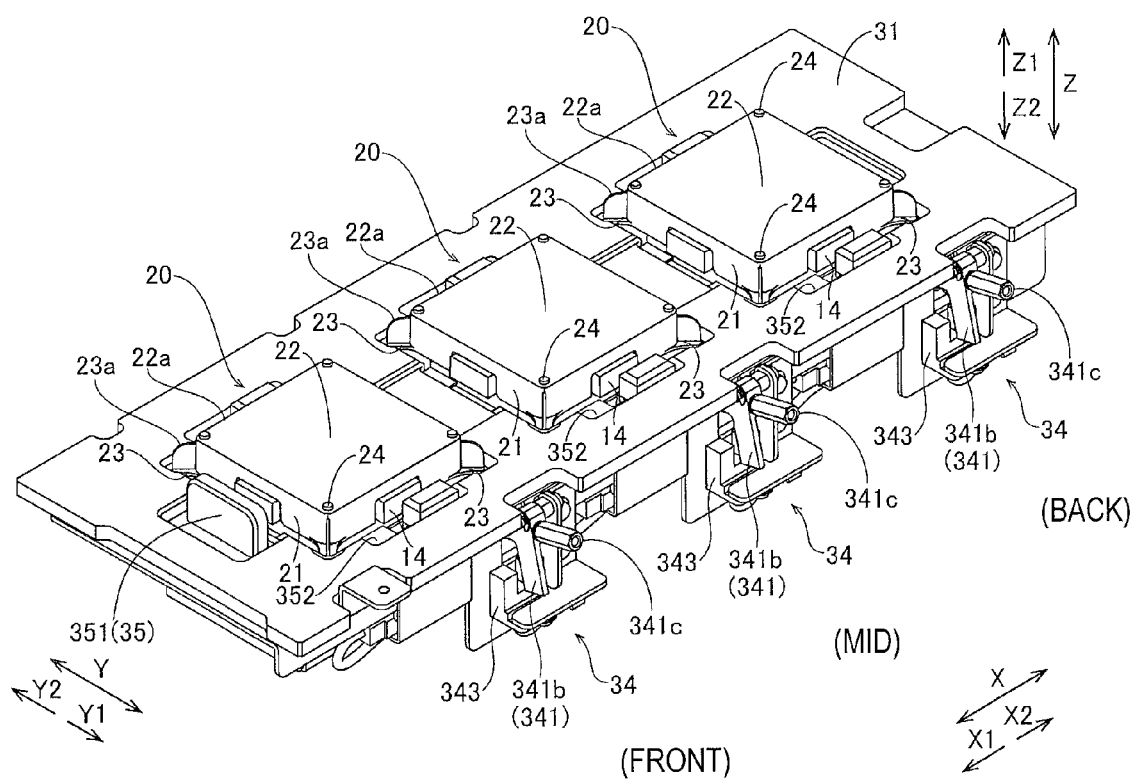
FIG. 11 shows the tip container mounted in the tip container mounting section of the gene amplification detecting apparatus of the first embodiment.
Figure 12:
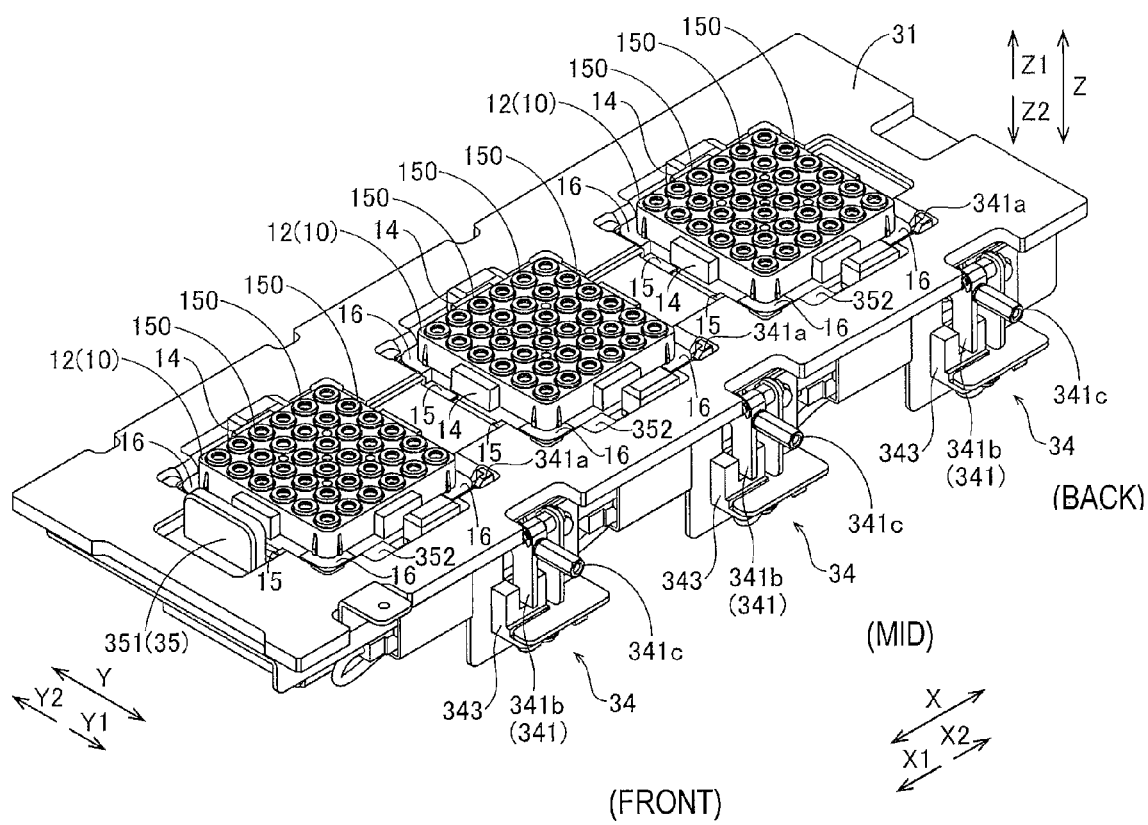
FIG. 12 shows the cover removed from the tip container mounted in the tip container mounting section of the gene amplification detecting apparatus of the first embodiment.

The open part 32 is substantially square in shape and corresponds to the tip container mounting body 10 in planar view. The tip container body 10 of the tip container 1 is accommodated in the open part 32, as shown in FIGS. 11 and 12. The open part 32 is configured so that the gripper 14 of the tip container body 10 and the side surface 21 of the cover 20 are exposed above the set rack 31 when the tip container 1 is accommodated.

Figure 13:
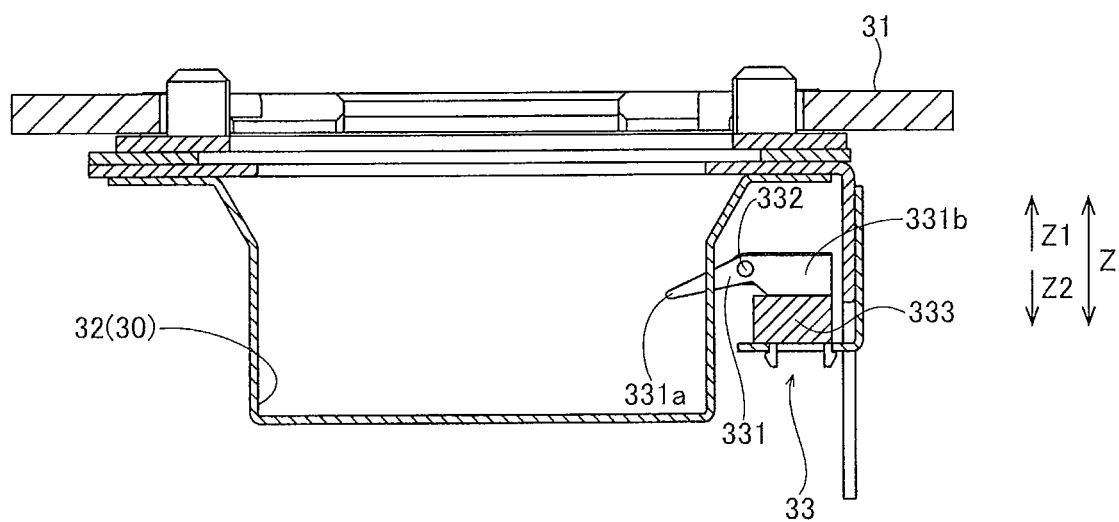
FIG. 13 shows the main detecting section when the tip container is not mounted in the gene amplification detecting apparatus of the first embodiment.
Figure 14:
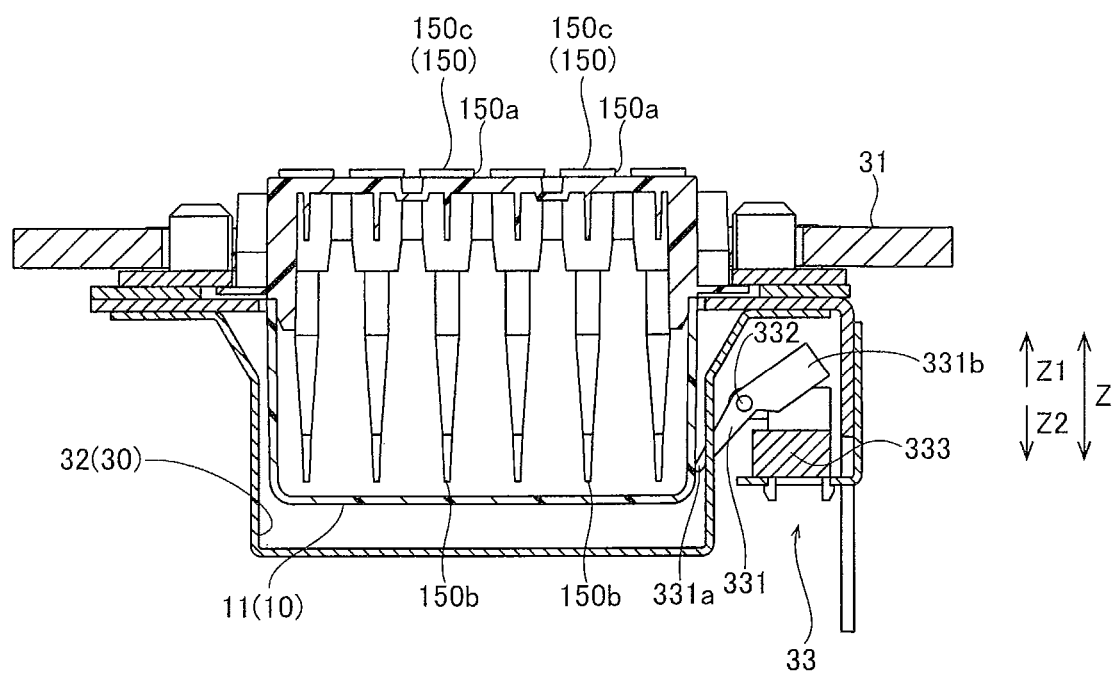
FIG. 14 shows the main detecting section when the tip container is mounted in the gene amplification detecting apparatus of the first embodiment.

The body detecting section 33 includes a lever 331, rotating shaft 332, and light sensor 333, as shown in FIGS. 13 and 14. One body detecting section 33 is provided in each of the three individual open parts 32. The body detecting section 33 is configured to detect the presence or absence of the tip container body 10 mounted in the tip container mounting section 30, that is, to detect whether a tip container body 10 is accommodated in the open part 32.

A single lever 331 is provided on the side part inside the open part 32. The lever 331 is configured to protrude toward the inside of the open part 32 from the inner side surface of the open part 32. The lever 331 is configured to pivot on the rotating shaft 332, and rotates when the end 331*a* comes into contact with the tip container body 10 when the tip container body 10 is accommodated in the open part 32. In this situation the other end 331*b* of the lever 331 does not block the light from the light sensor 333. Therefore, the CPU 90 detects that the tip container body 10 is accommodated in the open part 32. The body detecting section 33 and CPU 90 thereby detect whether a tip container body 10 is mounted in the tip container mounting section 30.

Figure 15:
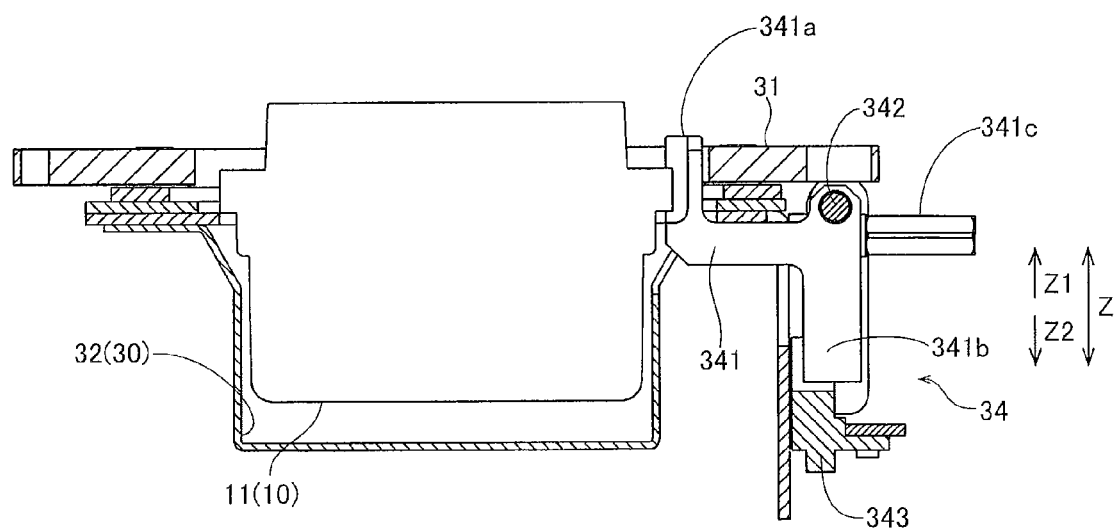
FIG. 15 shows the cover detecting section when the cover is not mounted on the tip container in the gene amplification detecting apparatus of the first embodiment.
Figure 16:
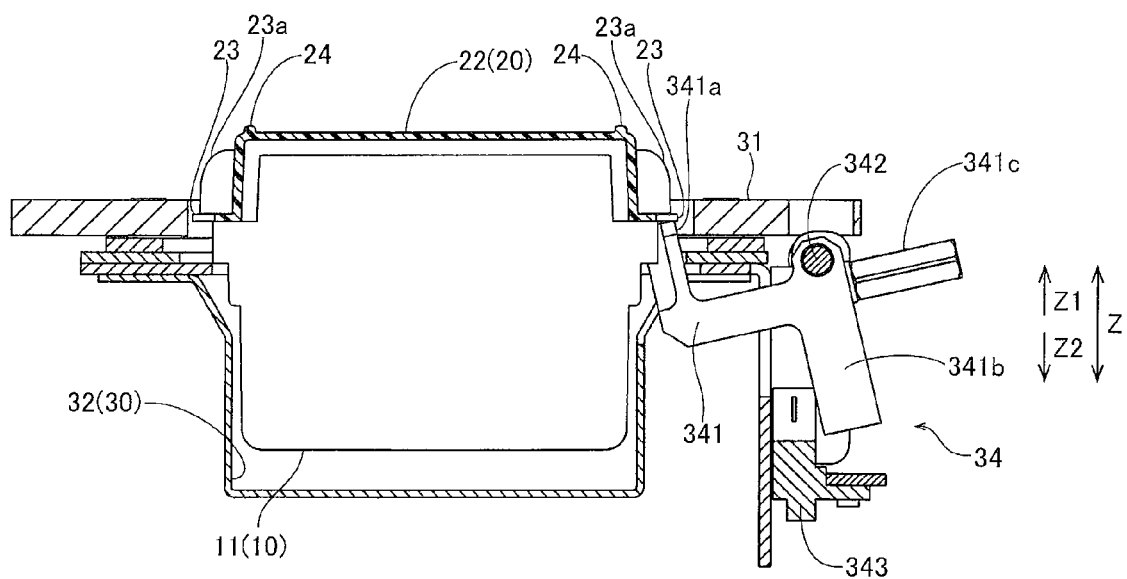
FIG. 16 shows the cover detecting section when the cover is mounted on the tip container in the gene amplification detecting apparatus of the first embodiment.

The cover detecting section 34 includes a lever 341, rotating shaft 342, and light sensor 343, as shown in FIGS. 15 and 16. One cover detecting section 34 is provided in each of the three individual open parts 32. The cover detecting section 34 is configured to detect the presence or absence of the cover 20 on the top part of the tip container body 10 mounted in the tip container mounting section 30, that is, to detect the whether the cover 20 is installed on the tip container body 10. Note that in the first embodiment the tip container body 1 mounted in the tip container mounting section 30 is used when the cover 20 is not installed on the top part.

A single lever 341 is provided at the corner of the open part 32. The lever 341 is configured to pivot on a rotating shaft 342. The lever 341 is configured to rotate when in the contact part 341*a* comes into contact with the detecting part 23 of the cover 20 when the cover 20 is mounted on the tip container body 10 accommodated in the open part 32. In this situation the shield part 341*b* of the lever 341 does not block the light from the light sensor 343. Therefore, the CPU 90 detects the presence of the cover 20 on the tip container body 10 accommodated in the open part 341. The cover detecting section 34 and the CPU 90 therefore detect whether the cover 20 is installed on the tip container body 10. When the cover 20 is removed from the tip container body 10, the lever 341 is rotated by the weight of the perpendicular part 341*c* provided on the opposite side from the contact part 341*a* via the rotating shaft 342.

As shown in FIG. 11, the fixing mechanism 35 includes a lever 351, and plate 352. The lever 351 is configured to move the plate 352 in the direction (X direction) in which the three open parts 32 are arranged. The plate 352 is configured to be slidable above the fixing part 15 of the tip container body 10 accommodated in the open part 32, between the fixing part 15 and the gripper 14 (see FIG. 4). Hence, the tip container body 10 accommodated in the open part 32 of the tip container mounting section 30 is prevented from rising up.

Each type of liquid container containing a predetermined liquid is mounted in the liquid container mounting section 40, as shown in FIG. 7. Specifically, the liquid container set holes 41*a* through 41*c* are provided in the liquid container mounting section 40 to hold liquid containers. A primer reagent container 42*b*, which contains cytokeratin (CK19) used as a primer, is disposed in the second liquid container set hole 41*b* from the innermost side (X2 direction side) of the gene amplification detecting apparatus 100. An enzyme reagent container 42*a* which contains cytokeratin enzyme reagent is disposed in the liquid container set hole 41*a* on the innermost side Sample containers 42*c* which contain solubilized extract as samples prepared through processing of excised tissue through homogenization, filtration, and dilution and the like, are disposed in the other 16 liquid container set holes 41*c*. A shutter member 43 which operates to open and close and is open when enzyme is dispensed from the enzyme reagent container 42*a*, is disposed near the liquid container set hole 41*a* which accommodates the enzyme reagent container 42*a*. The liquid container set holes 41*a* through 41*c* are spaced at predetermined distance from one another.

A plurality (eight in the first embodiment) of reaction detecting blocks 50*a* are provided in the reaction detecting section 50. The reaction detecting block 50*a* of the reaction detecting section 50 are configured by a reaction unit 51, turbidity detector (not shown in the drawings), and a cover mechanism 52. Each reaction unit 51 is provided with two detection cell set holes 51*a* for placement of detection cells 51*b*. The cover mechanism 52 is configured to be openable and closable so as to cover the detection cell 51*b* placed in the reaction unit 51.

The turbidity detecting unit includes an LED light which emits blue (wavelength: 465 nm) light as a light source, and a photodiode as a light receiver. Two turbidity detecting units are arranged in each reaction detection block 50*a*. The reaction detection block 50*a* of the reaction detecting section 50 is configured to detect the presence or absence of the detection cell 51*b* by the light receiver detecting the intensity of the light from the light source which irradiates the detection cell 51*b*, and detect and monitoring in real time the turbidity of the liquid in the detection cell 51*b*.

Figure 8:
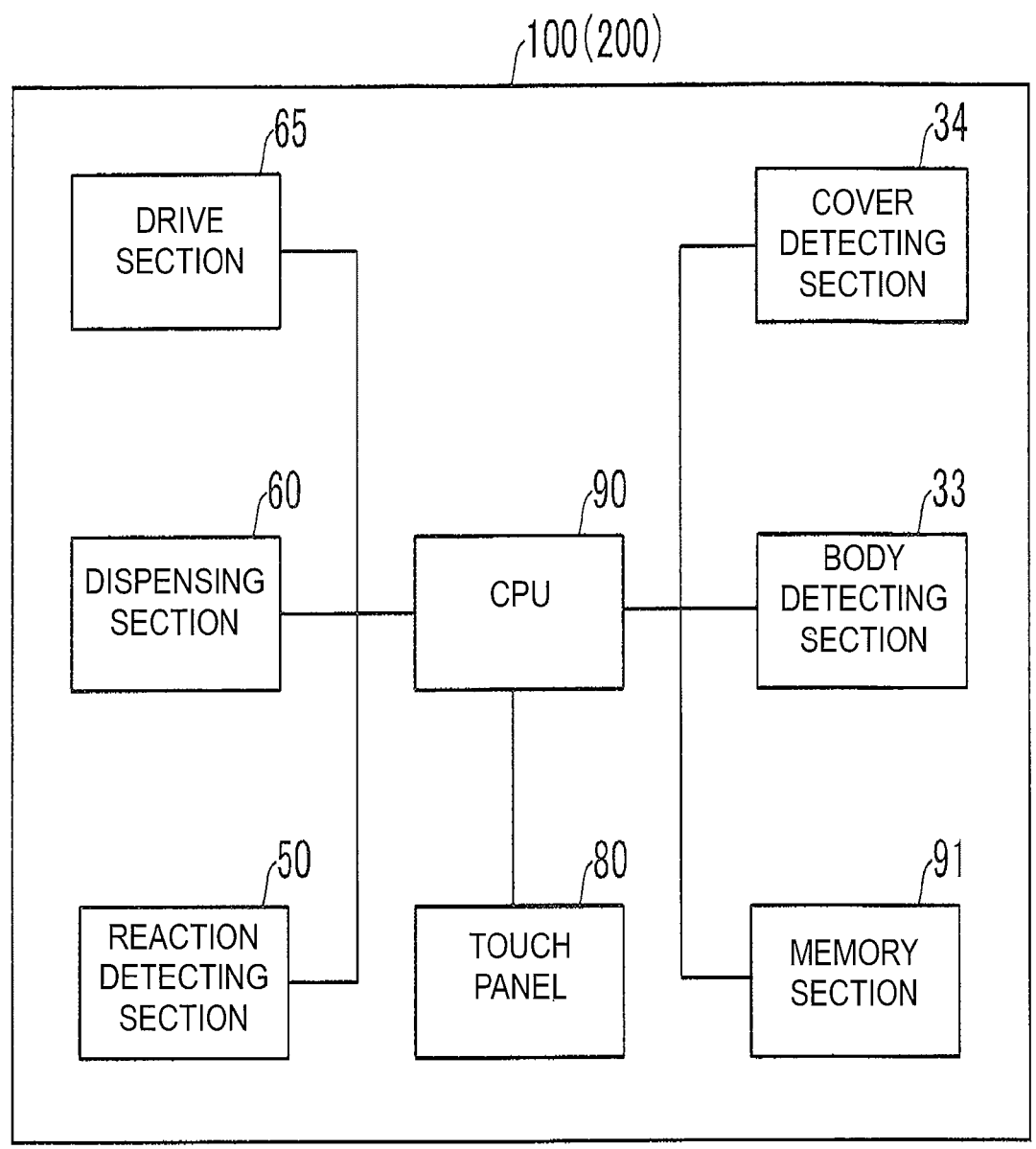
FIG. 8 is a block diagram of the gene amplification detecting apparatus of the first embodiment.

The dispensing section 60 is movable in the X direction and the Y direction by a belt driven by the drive unit 65 (see FIG. 8). The dispensing section 60 includes two syringe units 61 (see FIG. 17). The two syringe units 61 are movable in the Z direction (vertical direction) by a syringe elevator unit (not shown in the drawing). The dispensing section 60 is configured to removably install the tip 150 held in the tip container body 10. The dispensing section 60 aspirates and dispenses the liquid in the liquid containers (enzyme reagent container 42a, primer reagent container 42b, and sample containers 42c) through the installed tip 150.

Figure 17:
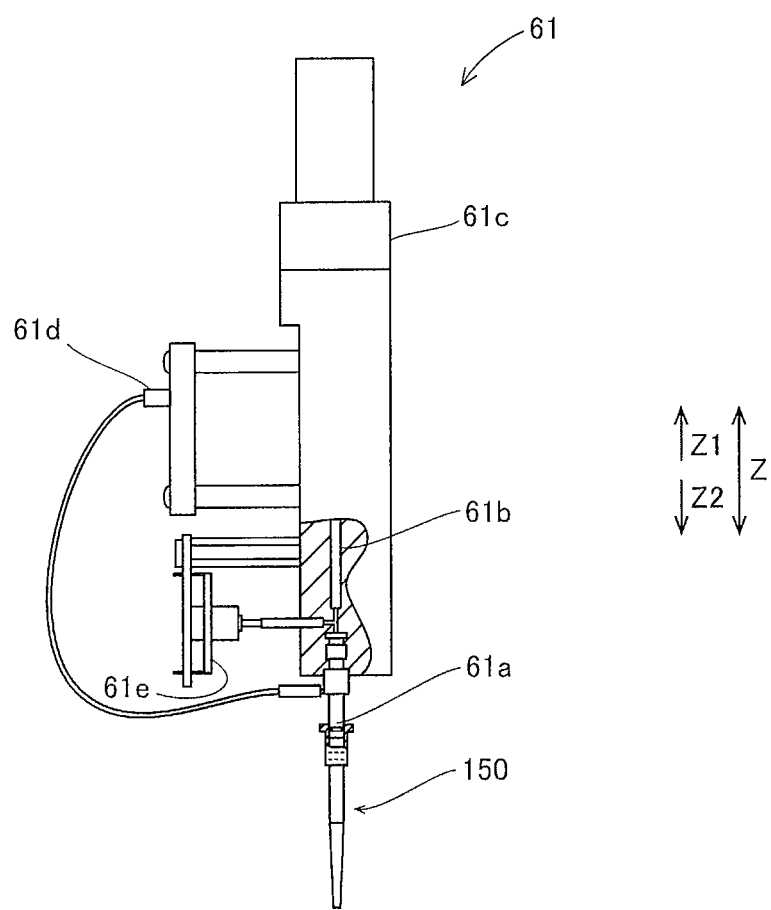
FIG. 17 shows the dispensing section of the gene amplification detecting apparatus of the first embodiment.
Figure 18:
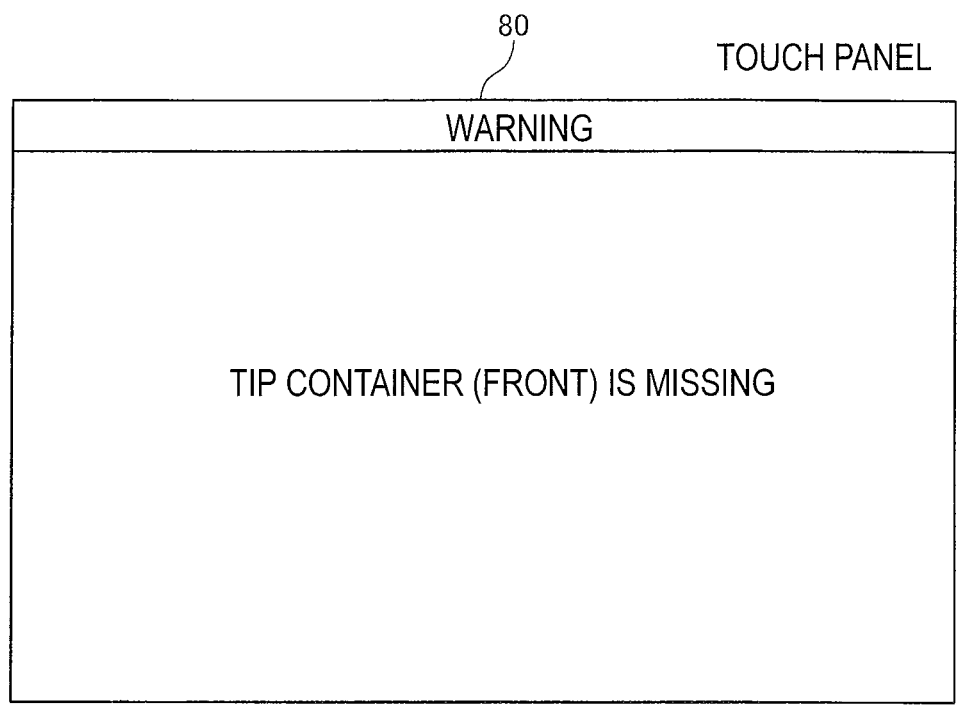
FIG. 18 shows the tip container mounting reminder screen of the gene amplification detecting apparatus of the first embodiment.
Figure 19:
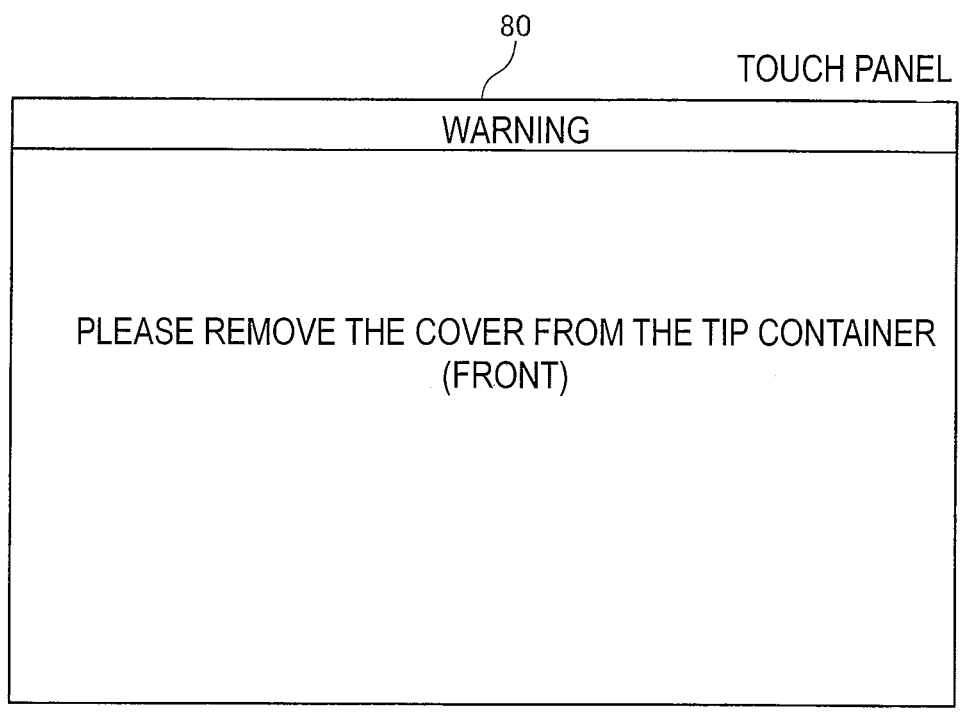
FIG. 19 shows the cover removal reminder screen of the gene amplification detecting apparatus of the first embodiment.

Specifically, the syringe unit 61 includes a nozzle 61a which is removably mounted on the tip 150, a pump unit 61b for aspirating and discharging, motor 61c for driving the pump unit 61b, capacitance sensor 61d, and pressure sensor 61e, as shown in FIG. 17. The syringe unit 61 aspirates and discharges by the changing the movement of a piston that rotates the motor 61c in the pump unit 61b. The capacitance sensor 61d detects the capacitance of the liquid and the tip 150 which is formed of conductive resin. The pressure sensor 61e detects the pressure during aspiration and discharge by the pump unit 61b. The capacitance sensor 61d and the pressure sensor 61e detect whether aspiration and discharge are reliably performed. In the first embodiment, the sequence of the installation of the tip 150 held in the tip container body 10 by the dispensing section 60 is predetermined. When the tip 150 is installed by the dispensing section 60, the dispensing section 60 starts the installation of the tip 150 from the next position when it was last used because the position of the installed tip is stored in the memory unit 91.

As shown in FIG. 7, the tip disposal section 70 has two tip disposal apertures 70a for discarding the used tips 150.

The touch panel 80 is provided on the front side (X1 direction side) of the gene amplification detecting apparatus 100. The touch panel 80 is configured to display predetermined information (for example, messages for the user). The touch panel 80 also receives information by user input (for example, instructions to start a measurement). Specifically, the user input operation is received by the touch panel 80 and the CPU 90.

The CPU 90 is configured to read the measurement process program from the memory section 91, such as a HDD, RAM or the like, and control the storage of the obtained information in memory section 91, as shown in FIG. 8. The CPU 91 (see FIG. 8) also is configured to control the operation of the dispensing section 60 based on the detection results of the body detecting section 33 and the cover detecting section 34 (hereinafter referred to simply as "detection results").

Specifically, the CPU 90 first determines whether a tip container body 10 is mounted in all three tip container mounting sections 30 based on the detection results of the body detecting section 33. When a tip container body 10 is not mounted in all three tip container mounting sections 30, the CPU 90 identifies the position of the tip container mounting section 30 which does not have a mounted tip container body 10 based on the detection results of the body detecting section 33. The CPU 90 then displays on the touch panel 80 the position information (for example, "front") identifying the tip container mounting section 30 which does not have a mounted tip container body 10, and a message prompting the user to mount a tip container 1 in the identified tip container mounting section 30.

The CPU 90 then determines whether a cover 20 is mounted on any tip container body 10 in the three installed tip container mounting sections 30 based on the detection results of the cover detecting section 34. The CPU 90 prohibits the operation of installing a tip 150 by the dispensing section 60 when at least one tip container body 10 has a mounted cover 20 among the three tip containers 1. The CPU 90 permits the operation of installing a tip 150 by the dispensing section 60 when it is determined that all tip container body 10 are without a mounted cover 20.

When a tip container body 10 has an installed cover 20 among the three tip containers 1, the CPU 90 identifies the position of the tip container body 10 which has the installed cover 20 based on the detection results of the cover detecting section 34. The CPU 90 then displays on the touch panel 80 a message including the position information identifying the tip container 1 which has the installed cover 20, and information prompting the removal of the cover 20.

The CPU 90 is configured to control the operation of the dispensing section 60 based on the detection results of the body detecting section 33 and the cover detecting section 34 when the touch panel 80 receives an instruction to start the measurement from the user.

The measuring operation performed by the gene amplification detecting apparatus 100 of the first embodiment is described below with reference to FIGS. 7, and 18 through 20. This process is executed by the CPU 90.

Figure 20:
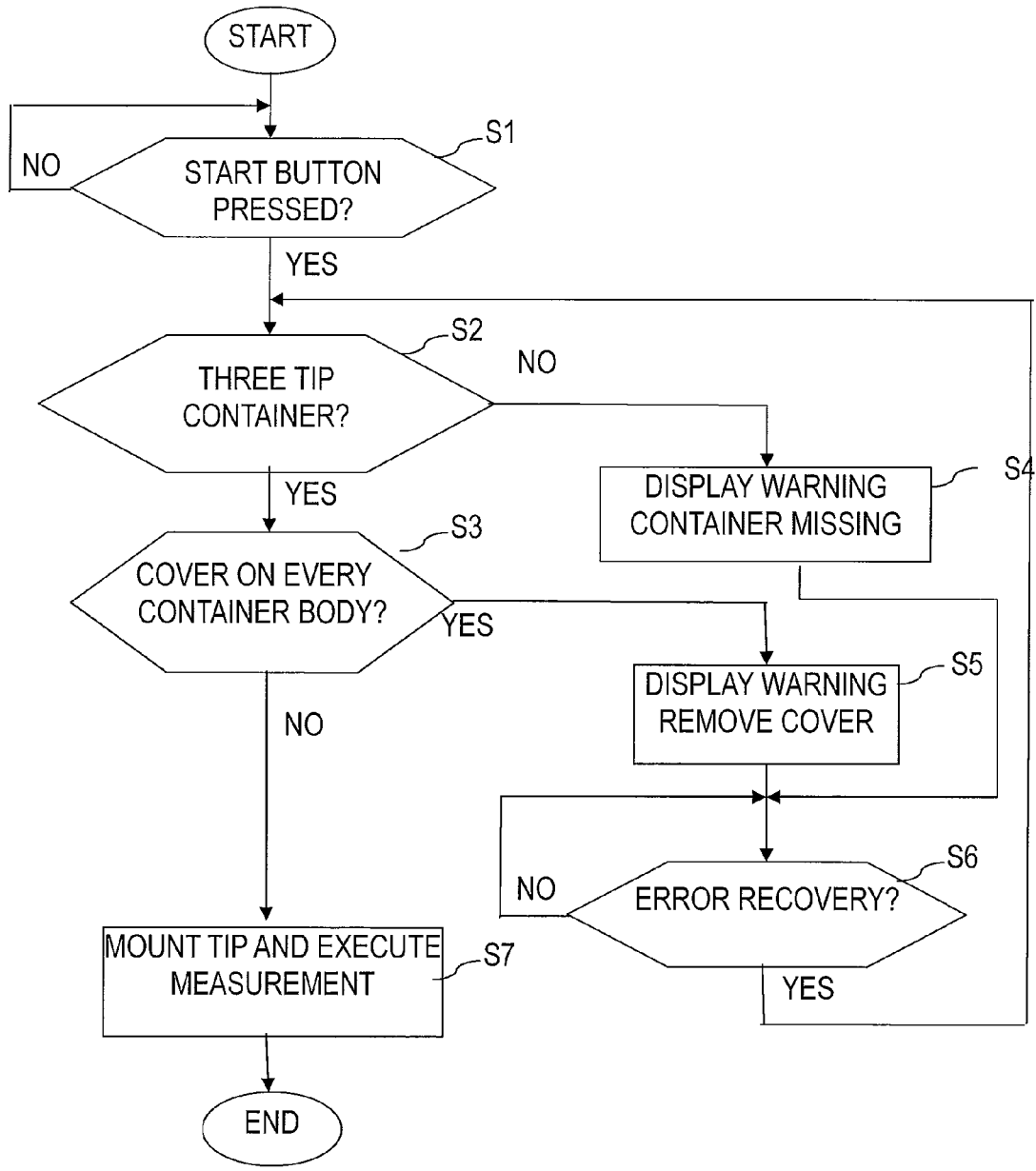
FIG. 20 is a flow chart illustrating the measurement process of the gene amplification detecting apparatus of the first embodiment.

As shown in FIG. 20, the CPU 90 first determines whether the measurement start button has been pressed in step S1. Specifically, the CPU 90 determines whether the user has pressed the measurement start button displayed on the touch panel 80 (see FIG. 7). The CPU 90 repeats the determination until the measurement start button is pressed; when the measurement start button is pressed, the CPU 90 advances the process to step S2.

In step S2, the CPU 90 determines whether all three tip containers 1 are mounted based on the detection results of body detecting section 33. When the three tip containers 1 are mounted in the respective tip container mounting sections 30, the CPU 90 advances the process to step S3. However, when the even one of the three tip containers 1 is not installed, the CPU 90 prohibits the operation of mounting the tip 150 by the dispensing section 60, identifies the position of the tip container mounting section 30 which lacks a mounted tip container body 10 based on the detection results of the body detecting section 33, and advances the process to step S4.

In step S3, the CPU 90 determines whether a cover 20 is mounted on any tip container body 10 among the three installed tip containers 1 based on the detection results of the cover detecting section 34. When at least one tip container body 10 has a mounted cover 20, the CPU 90 identifies the position of the tip container body 10 with the mounted cover 20 based on the detection results of the cover detecting section 34, and advances the process to step S5. When all tip container bodies are without a cover 20, the CPU 90 advances the process to step S7. Note that details of the tip installation and measurement processes executed in step S7 are described later.

In step S4, the CPU 90 displays a message indicating a tip container 1 is missing on the touch panel 80. Specifically, a reminder screen to mount the tip container (see FIG. 18) is displayed. This reminder screen, for example, shows a message such as "tip container (front) is missing". Thereafter, the CPU 90 advances the process to step S6. Thereafter, the CPU 90 advances the process to step S6.

In step S5, the CPU 90 prohibits the operation of mounting the tip 150 by the dispensing section 60, and displays on the touch panel 80 a message prompting the removal of the cover 20. Specifically, the cover removal reminder screen (see FIG. 19) is shown based on the detection results of the cover detecting section 34. The cover removal reminder screen, for example, shows a message such as "Please remove cover 20 from tip container (front)". Thereafter, the CPU 90 advances the process to step S6. Thereafter, the CPU 90 advances the process to step S6.

In step S6, the CPU 90 determines whether the apparatus has recovered from the error. Specifically, the when the process advances from step S4 to step S6, the CPU 90 determines whether the a tip container 1 is mounted in the tip container mounting section 30 identified as lacking a tip container 1 based on the detection results of the body detecting section 33. When the process advances from step S5 to step S6, the CPU 90 determines whether the cover 20 has been removed from the tip container body 10 identified as having a mounted cover based on the detection results of the cover detecting section 34. Note that the CPU 90 repeats the determinations until recovery from the error is completed; when the apparatus has recovered from the error, the process returns to step S2.

The tip installation and measurement processes in step S7 are summarized below with reference to FIG. 7.

In step S7, the dispensing section 60 first is moved from the initial position to above the (Z1 direction) the tip container mounting section 30. Thereafter, the two syringes 61 are lowered (Z2 direction) and the tips 150 are respectively installed on the leading end of the nozzle 61a (see FIG. 17) of the two syringes 61. The dispensing section 60 is then moved so that one syringe 61 is above the primer reagent container 42b, and this syringe 61 aspirates primer reagent. The dispensing section 60 is then moved so that the other syringe 61 is above the primer reagent container 42b, and this syringe 61 aspirates primer reagent.

After aspiration of the primer reagent, the dispensing section 60 is moved above the reaction detecting block 50a positioned at the innermost side (side in the X2 direction). At the reaction detecting block 50a, the syringes 61 are lowered and the primer reagent is respectively discharged into two detection cells 51b.

After the primer reagent has been discharged, the dispensing section 60 is moved above the tip discard section 70. The tips 150 are then inserted into the two tip disposal holes of the tip discard section 70. The dispensing section 60 is then moved in the Y1 direction, then raised upward. Thus, the collar 151b of the tip 150 is removed from each syringe 61 and discarded.

The dispensing section 60 then is again moved above the tip container mounting section 30 by the previously described operation, and tips 150 are installed on the leading ends of the nozzles 61a of the two syringes 61. The dispensing section 60 is then moved so that one syringe 61 is above the enzyme reagent container 42a, and this syringe 61 aspirates enzyme reagent. The dispensing section 60 is then moved so that the other syringe 61 is above the enzyme reagent container 42a, and this syringe 61 aspirates enzyme reagent. After aspiration of the enzyme reagent, the dispensing section 60 is moved above the reaction detecting block 50a at the innermost side, the syringes 61 are lowered into the reaction detecting block 50a, and the enzyme reagent is discharged from the tips 150 into two detection cells 51b. Then the tips 150 of the syringes 61 are discarded via the previously described operation.

The dispensing section 60 then is again moved above the tip container mounting section 30 by the previously described operation, and tips 150 are installed on the leading ends of the nozzles 61a of the two syringes 61. The dispensing section 60 is moved above the sample container 42c, and sample is aspirated from the sample container 42c through an operation identical to that of the aspirating operation of the primer reagent and enzyme reagent. The dispensing section 60 then is moved above the reaction detecting block 50a at the innermost side, the two syringes are lowered, and sample is discharged into the same two detection cells 51b. Note that when discharging the sample, the primer and enzyme reagents are mixed with the sample by repeated aspiration and discharge operations. Then the tips 150 of the syringes 61 are discarded via the previously described operation.

The cover mechanism 52 is closed after the primer reagent, enzyme reagent, and sample have been discharged into the detection cell 51b. The target nucleic acid (mRNA) is amplified by LAMP (nucleic acid amplification) reaction by heating the liquid in the detection cell 51b from approximately 20° C. to about 65° C. The turbidity caused by the magnesium pyrophosphate produced through amplification is detected (monitored) in real time through the light source and light receiver (not shown in the drawings), and the degree of turbidity is detected. Thereafter, the primer reagent, enzyme reagent, and sample are discharged sequentially into the reaction cell 51b of the reaction detecting block 50a, which is not at the innermost side, according to the number of samples to be measured, an turbidity is detected according to the LAMP reaction.

The following effects are obtained in the first embodiment.

In the first embodiment, the CPU 90 prohibits the operation of mounting the tip 150 by the dispensing section 60 when a cover 20 is installed on the top part of the tip container body 10 mounted in the tip container mounting section 30, and permits the operation of mounting the tip 150 by the dispensing section 60 when a cover 20 is absent from the top part of the tip container body 10. Thus, the generation of an error caused by the dispensing section 60 coming into contact with the cover 20 can be prevented even when the user starts a measurement while having forgotten to remove the cover 20 from the tip container body 10. As a result, there is no need to perform a process to recover from the error in order to restart the measurement, and there is no loss of time waiting to restart the measurement. Therefore, the measurement can be quickly restarted. A measurement also can be smoothly started without concern of generating an error.

In the first embodiment, the CPU 90 permits the operation of mounting the tip 150 by the dispensing section 60 when a cover 20 is absent from the top part of all the tip container bodies 10 mounted in the three tip container mounting sections 30, and prohibits the operation of mounting the tip 150 by the dispensing section 60 when a cover 20 is present on the top part of at least one tip container body 10 mounted in the three tip container mounting sections 30. A mounting operation also can be smoothly started without concern of generating an error. Error generation also can be reliably prevented when there is concern of generating an error.

In the first embodiment, the CPU 90 displays on the touch panel 80 a message prompting the removal of the cover 20 when a cover 20 is present on the top part of the tip container body 10 mounted in the tip container mounting section 30. Therefore, is user is easily notified that a cover 20 is on the tip container body 10. As a result, the user can quickly remove the cover 20 from the tip container body 10, and the operation to mount the tip 150 can be quickly restarted.

In the first embodiment, when a cover 20 is present on a tip container body 10 mounted in the tip container mounting section 30, the CPU 90 displays on the touch panel 80 the position information identifying the tip container body 10 which has the cover 20. Therefore, is user is easily notified which tip container body 10 has the cover 20. As a result, the user can quickly identify which tip container body 10 has a mounted cover 10 and remove the cover 20 from the tip container body 10, and the tip mounting operation can be quickly restarted.

In the first embodiment, the operation of mounting the tip 150 by the dispensing section 60 is prohibited when a cover 20 is installed on the top part of the tip container body 10 mounted in the tip container mounting section 30, and the operation of mounting the tip 150 by the dispensing section 60 is permitted when a cover 20 is absent from the top part of the tip container body 10 mounted in the tip container mounting section 30. The CPU 90 also prohibits the mounting operation of the tip 150 by the dispensing section 60 when a tip container body 10 is not mounted in a tip container mounting section 30. Therefore, it is possible to prevent an error generated by the dispensing section 60 performing the tip mounting operation when a tip container body 10 is not mounted in the tip container mounting section 30.

In the first embodiment, the CPU 90 either prohibits or permits the operation to mount the tip 150 by the dispensing section 60 when the touch panel 80 receives an instruction to start a measurement. Therefore, a measurement can be smoothly started without generating an error.

In the first embodiment, a protruding detecting part 23 is provided at all corners 20a of a substantially square shaped cover 20, and the presence or absence of any one among all detecting parts 23 is performed by the cover detecting section 34. Therefore, when the tip container body 10 is mounted in the tip container mounting section 30, the usability is improved for the user because the user need not be aware of the position of the detecting part 23 and the position of the cover detecting section 34. Note that the shape of the top surface of the cover 20 is not limited to being substantially square inasmuch as the top surface also may be a polygonal shape such as an approximate equilateral triangle or pentagon or the like.

In the first embodiment, the detecting part 23 is provided at a position lower than the tip surface of the cover 20 so as to protrude laterally from the cover 20. Therefore, the dispensing section 60 is prevented from contacting the detecting part 23 when the tip container body 10 is mounted in the tip container mounting section 30 since the detecting part 23 is not provided on the top side above the top surface 22 of the cover 20. The generation of an error is even more reliably prevented in this way.

In the first embodiment, four convexities 24 are provided near the inner surface of the side surface 21 of the cover 20, and the four convexities of one cover 20 mutually engage the side surface 21 of another cover 20 when a plurality of covers 20 are stacked. Therefore, a plurality of covers 20 can be stacked in a stable state when several covers 20 are stacked and stored.

In the first embodiment, the tip container body 10 includes a support 12 which supports the tip 150 while retaining it's detachability and has an insertion hole 13 for inserting a tip 150, and a holder 11 positioned below the support 12 to accommodate the end part 150b of the tip 150 inserted into the insertion hole 13 of the support 12; and the cover 20 is configured to cover the base 150c of the tip 150 which is inserted in the insertion hole 13 of the support 12. Contamination of the pipette tip by dust or the like is therefore more reliably prevented.

Second Embodiment

Figure 21:
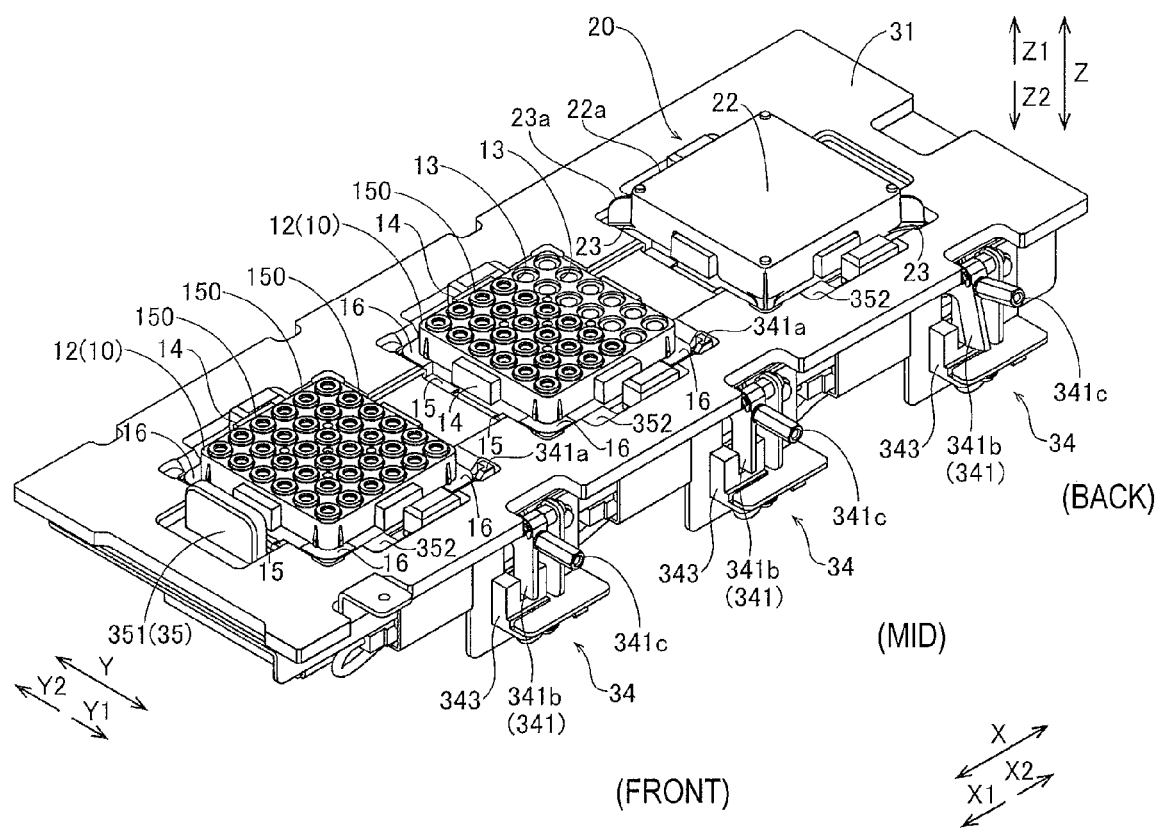
FIG. 21 shows the tip container from which tips have been used mounted in the gene amplification detecting apparatus of a second embodiment of the invention.
Figure 22:
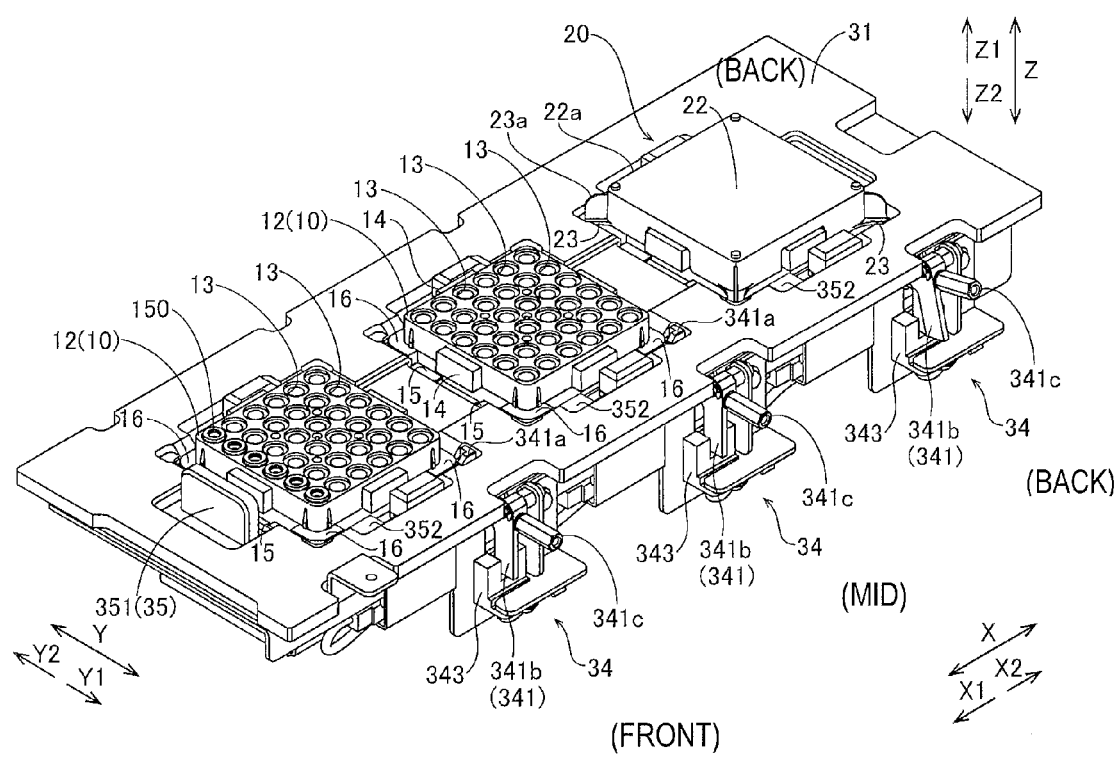
FIG. 22 shows the empty tip container mounted in the gene amplification detecting apparatus of the second embodiment.

The structure of the gene amplification detecting apparatus 100 of the second embodiment of the present invention is described below with reference to FIGS. 8, and 21 and 22.

In the second embodiment, the gene amplification detecting apparatus 200 is configured to be capable of detecting the number of tips 150 in addition to the presence and absence of the tip container 1 and the cover 20. In the following description, parts having the same reference numbers as the first embodiment are identical to the first embodiment and further description is omitted.

In the second embodiment, the CPU 90 (see FIG. 8) is configured to be capable of detecting the number of tips 150 accommodated in the tip container body 10. Specifically, the CPU 90 calculates the number of tips 150 remaining at the current time by calculating the difference between the number of used tips 150 and the number of tips 150 previously loaded in the tip container body 10. This calculation is executed by assuming the tip container body 10 is a new part when mounted in the tip container mounting section 30. Note that the information on the used tips 150 is stored in the memory section 91 each time an operation is performed by the dispensing section 60 of mount the tip 150.

The measuring process performed by the gene amplification detecting apparatus 200 of the second embodiment is described below with reference to FIGS. 18, 19, and 21 through 25. This process is executed by the CPU 90. Note that the processes of steps identified by the same reference numbers as in the first embodiment are identical to those of the first embodiment and further description is omitted.

Figure 25:
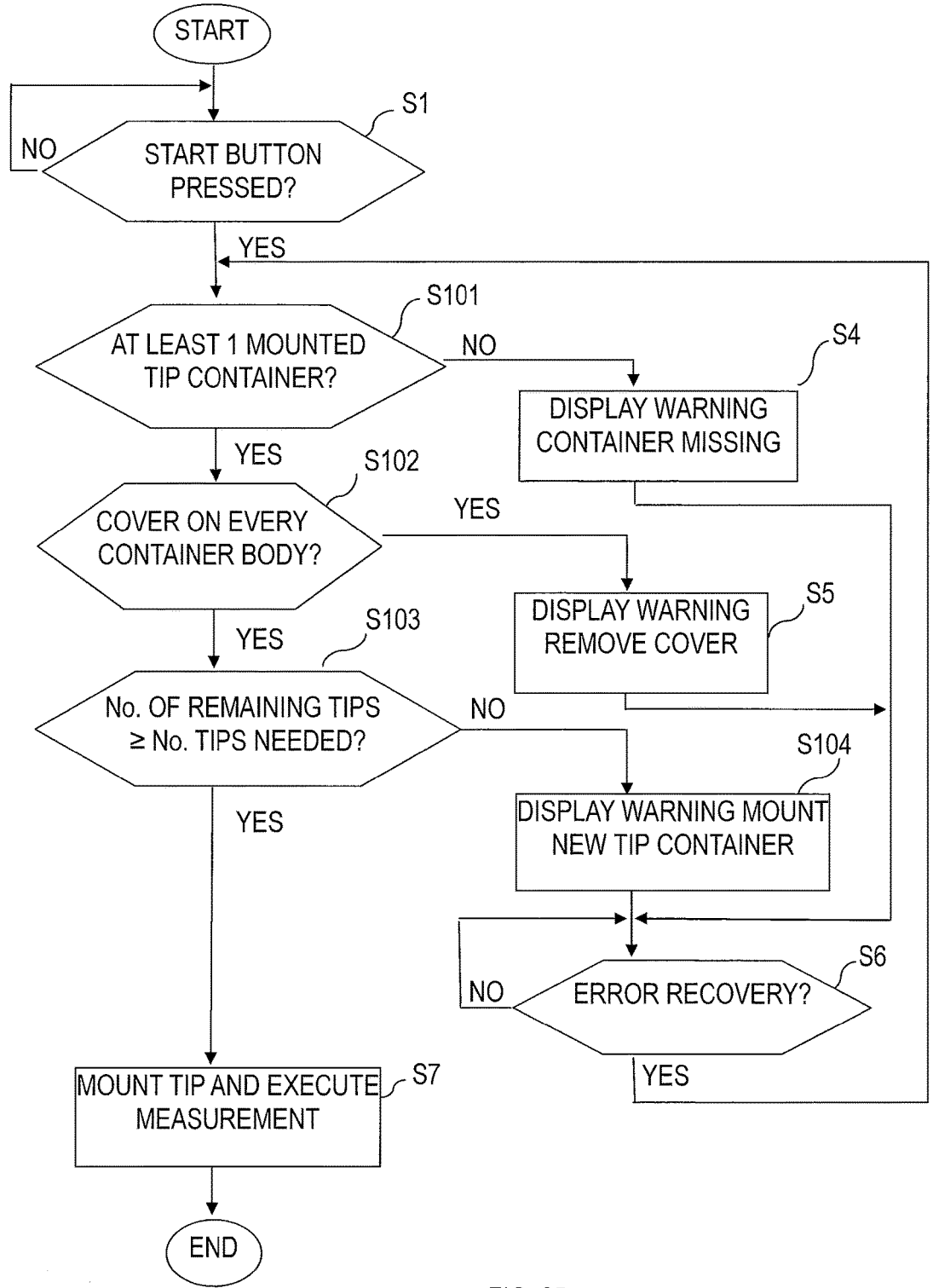
FIG. 25 is a flow chart illustrating the measurement process of the gene amplification detecting apparatus of the second embodiment.

As shown in FIG. 25, after the measurement start button is pressed, the CPU 90 determines whether a tip container mounting section 30 loaded with tip container 1 is present based on the detection results of the body detecting section 33 in step S101. When at least one tip container mounting section 30 has a mounted tip container 1, the CPU 90 identifies the position of the tip container mounting section 30 with the mounted tip container 1 based on the detection results of the body detecting section 33, and advances the process to step S102. When not even one tip container mounting section 30 has a mounted tip container 1, the CPU 90 advances the process to step S4. In this case, a message such as "There are no tip containers" (see FIG. 18) is displayed on the reminder screen to mount a tip container in step S4.

In step S102, the CPU 90 determines whether covers 20 are installed on every mounted tip container 1. When a cover 20 is installed on every mounted tip container 1, the CPU 90 advances the process to step S5. The cover removal reminder screen, for example, shows a message such as "Please remove cover 20 from tip container (front)" in step S5. However, when a cover 20 is installed on every mounted tip container 1, that is, when at least one tip container 1 does not have an installed cover 20 among the mounted tip containers 1, the CPU 90 advances the process to step S103.

In step S103, the CPU 90 calculates the number of tips 150 remaining at the current time by calculating the difference between the number of used tips 150 and the number of tips 150 previously loaded in the tip container body 10, and determining whether the calculated number of tips 150 is equal to or greater than number needed for the dispensing operation. When the number of tips 150 is equal to or greater than the number required, the CPU 90 advances the process to step S7. However, when the number of tips 150 is less than the estimated number required, the CPU 90 advances the process to step S104.

Figure 23:
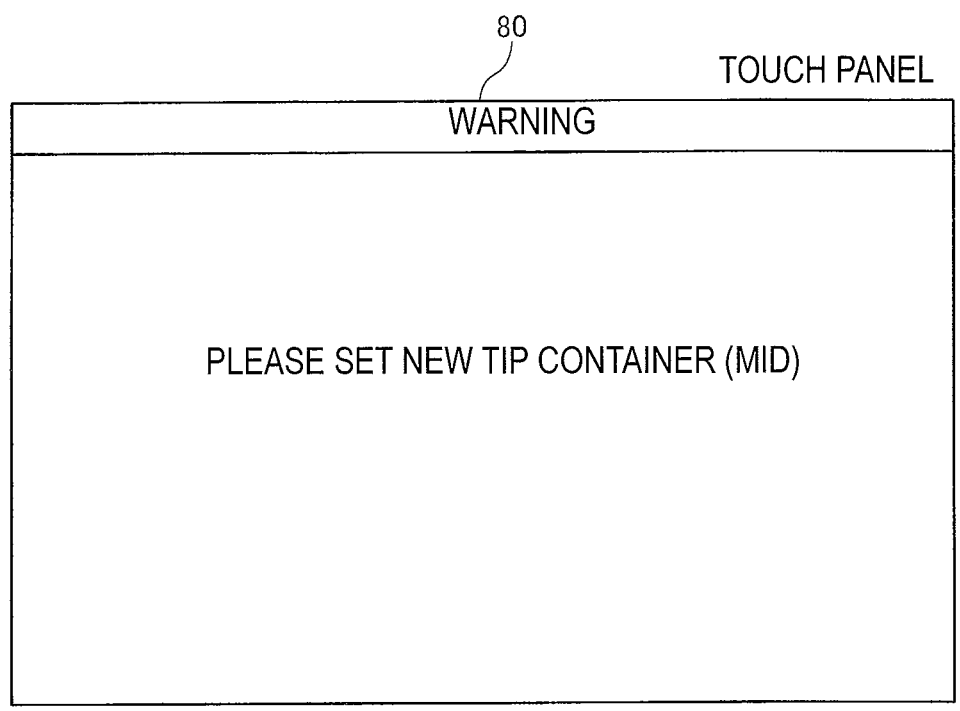
FIG. 23 shows the tip container replacement reminder screen of the gene amplification detecting apparatus of the second embodiment.
Figure 24:
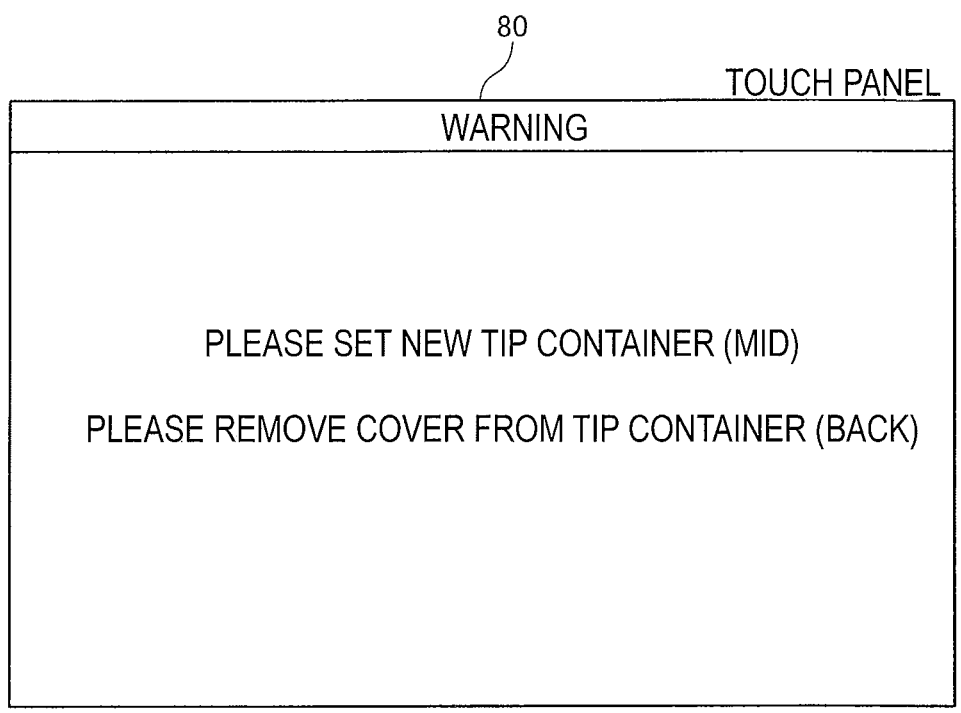
FIG. 24 shows another tip container replacement reminder screen of the gene amplification detecting apparatus of the second embodiment.

In step S104, the CPU 90 prohibits the operation of mounting the tip 150 by the dispensing section 60, and displays a message on the touch panel 80 prompting the mounting of a new tip container 1. In the second embodiment, a tip container replacement screen is displayed which includes a message to ensure that the estimated number of needed tips 150 are available. As shown in FIGS. 23 and 24, the tip container replacement screen shows a message "Please install a new tip container (mid) prompting the replacement of the depleted tip container body 10 which does not have the needed number of tips 150 or has none with a new tip container body 10. In this case, a message suggesting the removal of the cover 20 also may be displayed when a tip container body 10 with an installed cover 20 is mounted in the tip container mounting section 30, as shown in FIG. 24. When a plurality of tip containers 1 have remaining tips 150, the position (front, mid, back) of the tip container mounting section 30 with the newly replaced tip container 1 is determined to minimize the number of wasted tips 150 in step S104. Thereafter, the CPU 90 advances the process to step S6. Thereafter, the CPU 90 advances the process to step S6.

When the process advances to step S7, the tip mounting and measurements are performed identically to the first embodiment, then the CPU 90 ends the measurement process.

Other structures of the second embodiment are identical to those of the first embodiment.

The following effects are obtained in the second embodiment.

In the second embodiment, the CPU 90 prohibits the operation of mounting the tip 150 by the dispensing section 60 when a cover 20 is installed on the top part of every mounted the tip container body 10, and permits the operation of mounting the tip 150 by the dispensing section 60 when a cover 20 is absent from the top part of at least one mounted tip container body 10. Accordingly, error generation is reliably prevented when the tip mounting operation is started and the user has forgotten to remove the cover 20 from all the tip container bodies 10. The tip mounting operation also can be smoothly started even when the tip mounting operation is started when the user has forgotten to remove the cover 20 from only some of the tip container bodies 10.

In the second embodiment described above, the CPU 90 is configured to prohibit the operation of mounting the tip 150 by the dispensing section 60 when a cover 20 is absent from the top part of at least one mounted tip container body 10 but the number of tips 150 accommodated in the tip container body 10 that lacks the cover 20 is less than the number needed, and permit the operation to mount the tip 150 by the dispensing section 60 when the number of tips 150 accommodated in the tip container body 10 that lacks the cover 20 is equal to or greater than the number needed. Therefore, interruption of the mounting operation due to an insufficient number of tips 150 is prevented during the operation to mount the tip 150. Further, when there is a sufficient number of tips 150, the tip mounting operation is smoothly started.

Note that other effects of the second embodiment are identical to those of the first embodiment.

Note that the embodiments of the present disclosure are examples in all aspects and not to be considered limiting in any way. The scope of the present invention is expressed by the scope of the claims and not by the description of the embodiment, and includes all meanings and equivalences and modifications pertaining thereunto.

For example, although the sample analyzer of the present invention is described by way of example applied to a gene amplification detecting apparatus 100 and 200 in the first and second embodiments, the present invention is not limited to these examples. The sample analyzer of the present invention also is applicable to sample analyzers other than the gene amplification detecting apparatuses 100 and 200.

Although the CPU 90 is configured to prohibit or permit the mounting operation of the pipette 150 by the dispensing section 60 when a measurement start input operation is received from the touch panel 80 in the first and second embodiments, the present invention is not limited to this configuration. For example, the CPU 90 also may prohibit or permit the mounting operation of the pipette 150 by the dispensing section 60 when a record of measurement items is received from the touch panel 80. According to this configuration, measurement can be smoothly started without generating an error by prohibiting or permitting the mounting operation of the pipette 150 by the dispensing section 60 by the timing of the recording of measurement items by the user.

Although the first and second embodiments are described by way of examples providing three tip container mounting sections, the present invention is not limited to these examples. In the present invention, one two, or four or more tip container mounting sections may be provided.

Although the first and second embodiments are described by way of examples providing four cover detection parts, the present invention is not limited to these examples. In the present invention, one two, or four or more cover detection parts may be provided.

Although the first and second embodiments describe examples in which the detection parts protrude laterally form the cover, the present invention is not limited to this configuration. In the present invention, the detection parts also may protrude from the top surface of the cover.

Although the first and second embodiments describe example in which the top surface of the cover is substantially square in planar view, the present invention is not limited to this shape. In the present invention, the top surface of the cover also may be a polygonal shape with point symmetry relative to the center point (for example, rectangular) in planar view rather than square. In this case, it is preferable that the protruding detection part is provided at least at a mutually opposed pair of corners among the corners of the cover, and the cover detecting section detects the presence or absence of any one of the plurality of detection parts provided on the cover. In this way the usability is improved for the user because the user need not be aware of the position of the detecting part and the corresponding detecting section compared to when the detection part is provided on only one corner when the tip container is mounted in the tip container mounting section.

Although the first embodiment describes an example in which the measurement process is executed when tip container bodies are mounted in all tip container mounting sections, the present invention is not limited to this configuration. In the present invention, the measurement process also may be executed when a tip container body is mounted in at least one tip container mounting section.

In the first and second embodiments, the provided cover detecting section and body detecting section are mechanical types which have a rotation mechanism, however, the present invention is not limited to this configuration. In the present invention, the cover detecting section and the body detecting section may be a non-mechanical type such as, for example, an electrical type.

The second embodiment is described by way of example in which the number of tips accommodated in the tip container body is determined indirectly by calculating the difference between the number of tips previously mounted in the tip container body mounting in the tip container mounting section and the number of tips already used, however, the present invention is not limited to this configuration. In the present invention, the number of tips also may be obtained directly using a light source device such as a laser or an imaging device such as a camera. For example, when the tip container body is configured by a translucent material and the tip is configured by a non-translucent material, the number of tips can be obtained by calculating the number of shadows based on information obtained by irradiating light from below or above on the tip container body.

Although the first and second embodiments are described using a flow-driven flow for performing processes sequentially along the processing flow of the controller to facilitate understanding, the processes of the controller also may be performed by an event-driven process which executes processes in event units. In this case, complete processes may be event-driven or a combination of event-driven and flow-driven.

Although the cover 20 is configured to be removably mounted on the top part of the tip container body 10 in the first and second embodiments, the present invention is not limited to this configuration. For example, the cover 20 may be provided to open and close the top part of the tip container body 10.

What is claimed is:

1. An analyzer comprising:
a liquid container mounting section configured to set a liquid container;
a tip container mounting section comprising at least one tip container accommodating a plurality of pipette tips and a cover mounted on the tip container,
wherein the cover comprises a plurality of corners, wherein detection parts are provided on each corner of the cover, and wherein each detection part extends laterally from a side surface of the cover;
a cover detecting section arranged at positions corresponding to the detection parts and detecting a presence or absence of the detecting parts, wherein the cover detecting section is positioned lower than a top surface of the cover;
a dispensing section that equips a pipette tip accommodated in the tip container and dispenses a quantity of liquid from the liquid container to a reaction container via the equipped pipette tip;
a detecting section that interrogates a property of the liquid; and
a controller programmed to prohibit a process of equipping the pipette tip by the dispensing section when the cover on the tip container is detected, and permits the process when no cover is detected.

2. The analyzer of claim 1, wherein two or more tip containers are set in the tip container mounting section,
wherein the controller is programmed to permit the process when no cover is detected with respect to all of the tip containers, and prohibit the process when at least one cover is detected.

3. The analyzer of claim 1, wherein two or more tip containers are set in the tip container mounting section,
wherein the controller is programmed to prohibit the process when it is detected that all of the tip containers are covered, and permit the process when it is detected that at least one tip container is not covered.

4. The analyzer of claim 3,
wherein the controller is further programmed to:
calculate a number of pipette tips accommodated in each of the tip containers,
prohibit the process when it is detected that at least one tip container is uncovered but the number of pipette tips accommodated in the tip container which has been detected to be uncovered is less than a predetermined required number, and
permit the process when the number of pipette tips is equal to or greater than the predetermined required number.

5. The analyzer of claim 1 further comprising:
an output section, wherein
the controller is programmed to output information prompting a removal of the cover to the output section when a cover on the tip container is detected.

6. The analyzer of claim 2 further comprising:
an output section comprising a display, wherein
the controller is programmed to control the display to display information identifying the tip container which has a cover when at least one cover is detected.

7. The analyzer of claim 1, further comprising:
a main body detecting section that detects the tip container mounted in the tip container mounting section; wherein
the controller is programmed to
prohibit the process when no tip container is detected;
prohibit the process when a tip container is detected and the cover on the tip container is also detected; and
permit the process when a tip container is detected and no cover on the tip container is detected.

8. The analyzer of claim 1, wherein
the cover is configured to be removable from the top part of the tip container.

9. The analyzer of claim 1, further comprising:
a touch panel for receiving an instruction to start an operation;
wherein the controller is programmed to make the cover detecting section detect the cover of the tip container in response to the instruction, and permit or prohibit the process according to the presence of the cover.

10. The analyzer of claim 1, wherein
the controller is programmed to make the cover detecting section detect the cover of the tip container in response to a measurement start input, and permit or prohibit the process according to the presence of the cover.

* * * * *